(12) United States Patent
Marche et al.

(10) Patent No.: US 10,371,619 B2
(45) Date of Patent: Aug. 6, 2019

(54) POROSIMETRY TRANSITION REGION ADJUSTMENT

(71) Applicant: Schlumberger Technology Corporation, Sugar Land, TX (US)

(72) Inventors: Olivier Marche, Grabels (FR); Andrey Vladimirovich Kazak, Moscow (RU); Keith Pinto, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 190 days.

(21) Appl. No.: 15/545,720

(22) PCT Filed: Jan. 26, 2016

(86) PCT No.: PCT/US2016/014883
§ 371 (c)(1),
(2) Date: Jul. 23, 2017

(87) PCT Pub. No.: WO2016/130314
PCT Pub. Date: Aug. 18, 2016

(65) Prior Publication Data
US 2018/0010996 A1 Jan. 11, 2018

(30) Foreign Application Priority Data
Feb. 11, 2015 (FR) ...................... 15 51096

(51) Int. Cl.
*G01N 15/00* (2006.01)
*G01N 15/08* (2006.01)

(52) U.S. Cl.
CPC ..... *G01N 15/0886* (2013.01); *G01N 15/0826* (2013.01); *G01N 2015/0813* (2013.01); *G01N 2015/0853* (2013.01)

(58) Field of Classification Search
CPC .... G01N 15/00; G01N 15/08; G01N 15/0826; G01N 15/0886; G01N 2015/0813; G01N 2015/0853
See application file for complete search history.

(56) References Cited

U.S. PATENT DOCUMENTS

| 4,211,106 A | 7/1980 | Swanson |
| 4,644,779 A * | 2/1987 | Sisti .................. G01N 15/0886 73/38 |

(Continued)

FOREIGN PATENT DOCUMENTS

| EP | 0201118 A2 | 11/1986 |
| EP | 0653619 A1 | 5/1995 |

OTHER PUBLICATIONS

Kazak, et al., "Mercury Porosimetry of Core Samples: Experimental Aspects. A Case Study of a Dolomite Reservoir, East Siberia," GeoBaikal 2014, Aug. 22, 2014, pp. 18-22.

(Continued)

*Primary Examiner* — Nguyen Q. Ha
(74) *Attorney, Agent, or Firm* — Gary Gex

(57) ABSTRACT

A method can include receiving porosimetry data for a range of pressures that spans a transition zone defined at least in part by a high-pressure end of a first pressure zone and a low-pressure end of a second pressure zone; detecting at least one artifact in the transition zone; computing accuracy information for the high-pressure end of the first pressure zone and the low-pressure end of the second pressure zone; computing a pressure-volume adjustment based at least in part on the accuracy information; and outputting a pressure-volume relationship in the transition zone based at least in part on the pressure-volume adjustment.

20 Claims, 16 Drawing Sheets

(56) References Cited

U.S. PATENT DOCUMENTS

| | | | |
|---|---|---|---|
| 7,421,885 B2 * | 9/2008 | Kitzhoffer | G01N 15/0893 702/43 |
| 2005/0216223 A1 | 9/2005 | Lenormand et al. | |
| 2006/0070425 A1 | 4/2006 | Lasswell et al. | |
| 2007/0062258 A1 | 3/2007 | Egermann et al. | |
| 2011/0167897 A1 * | 7/2011 | Huang | G01N 15/088 73/38 |
| 2014/0366621 A1 | 12/2014 | Valenza et al. | |
| 2015/0000377 A1 * | 1/2015 | Qajar | G01N 15/088 73/38 |

OTHER PUBLICATIONS

Extended Search Report for the equivalent European patent application 16749583.7 dated Nov. 6, 2018.

Andersen et al., "Core Truth in Formation Evaluation," Oilfield Review, Summer 2013, 25, No. 2, pp. 16-25.

Comisky, et al., "Sample size effects on the application of mercury injection capillary pressure for determining the storage capacity of tight gas and oil shales," Canadian Unconventional Resources Conference, Society of Petroleum Engineers, 2011, pp. 1-21.

Micromeritics, Mercury Intrusion Porosimetry Theory, 2007.

Micromeritics, Porosimetry Brochure, 2001.

Sigal, "A methodology for blank and conformance corrections for high pressure mercury porosimetry," Measurement Science and Technology, 2009, vol. 20, No. 4, 045108, pp. 1-11.

Washburn et al., "Note on a Method of Determining the Distribution of Pore Sizes in a Porous Material," Proceedings of the National Academy of Sciences of the United States of America, vol. 7, 1921, pp. 115-116.

International Search Report and Written Opinion for the equivalent International patent application PCT/US2016/014883 dated May 13, 2016.

International Preliminary Report on Patentability for the equivalent International patent application PCT/US2016/014883 dated Aug. 24, 2017.

\* cited by examiner

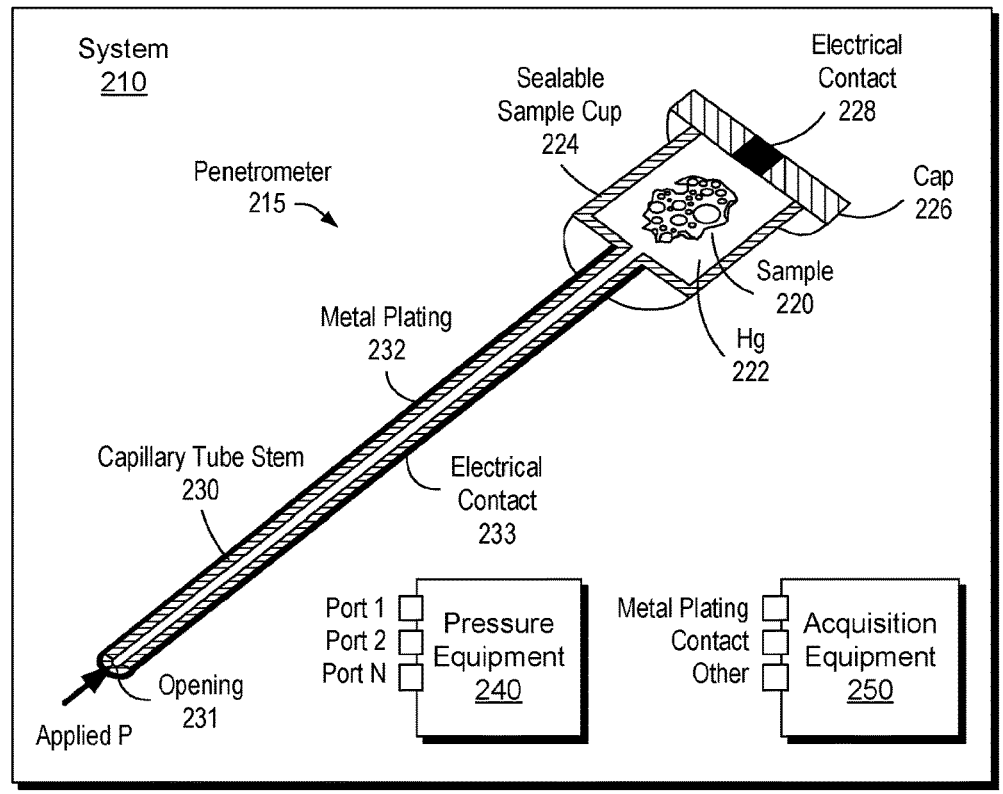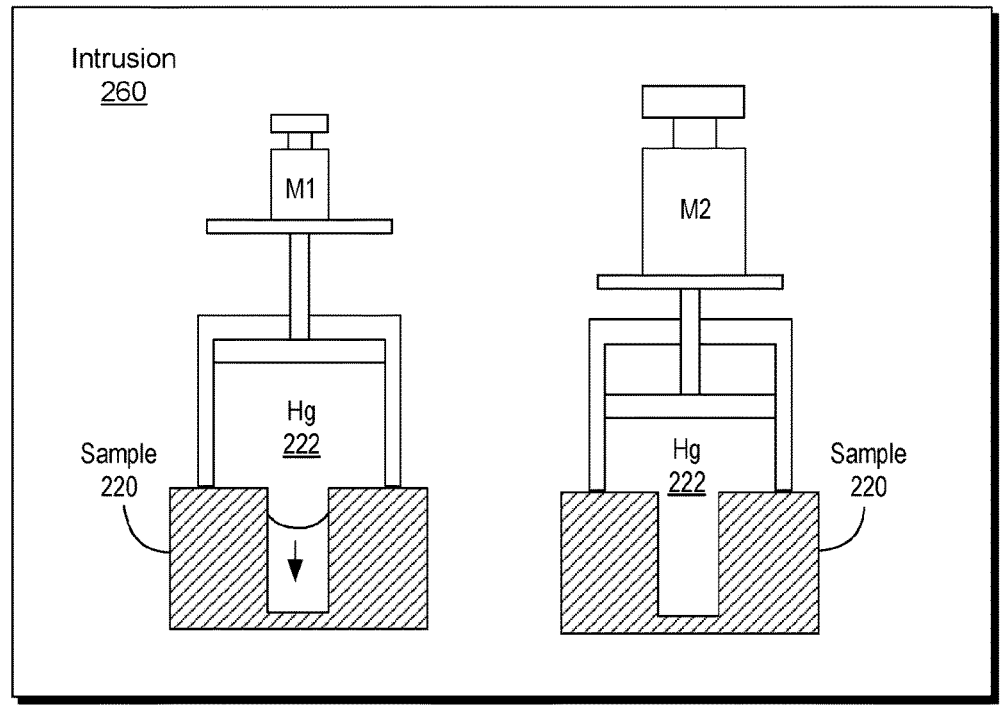
Fig. 2

Method 300
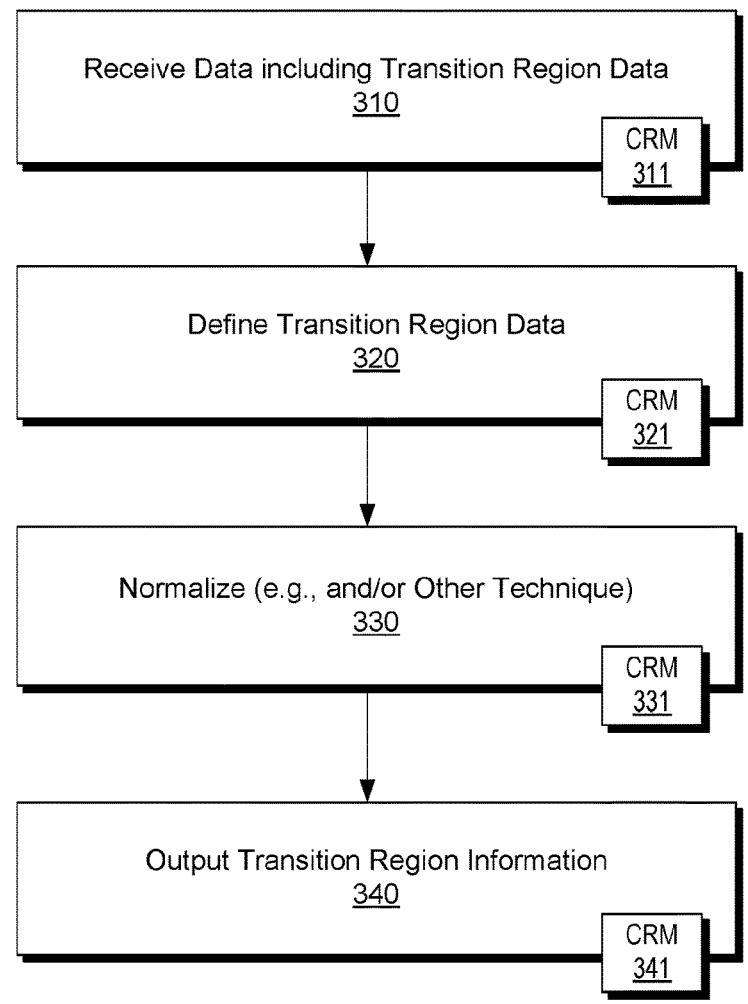
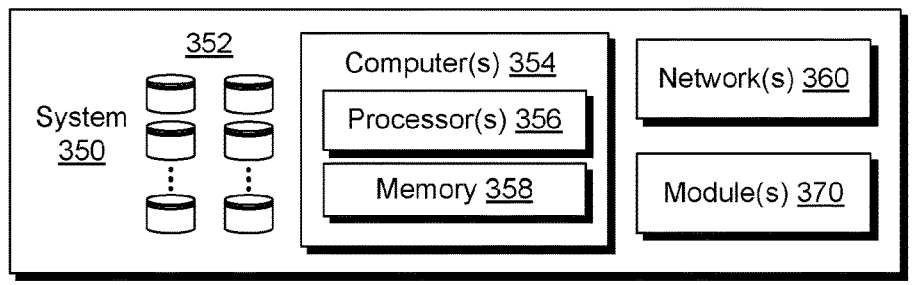
Fig. 3

GUI 410

| Project | Home | Plot | Data | Utility | Petrophysics | Geology | Geomechanics | Drilling | Reservoir | Geophys | Unconventional |
|---------|------|------|------|---------|--------------|---------|--------------|----------|-----------|---------|----------------|

- ☐ Grain size analysis
- ☐ Stress computation
- ☐ Petrophysics groups
- ☐ Petrophysics log
- ☐ Stress correction 420 — Read 2D array data / Capillary pressures / Core build / Log apply / Pc modeling Techcore

440

| | |
|---|---|
| Resampling | Ctrl+Shift... |
| Pressure transition artifact reduction | Ctrl+Shift... |
| Closure correction... | Ctrl+Shift... |
| Stress correction... | Ctrl+Shift... |
| Clay bound water correction... | Ctrl+Shift... |
| Pressure transformations... | Ctrl+Shift... |
| Computation of J – Leverett... | Ctrl+Shift... |
| Hyperbolic tangent method... | Ctrl+Shift... |
| WWJ method... | Ctrl+Shift... |

Fig. 4

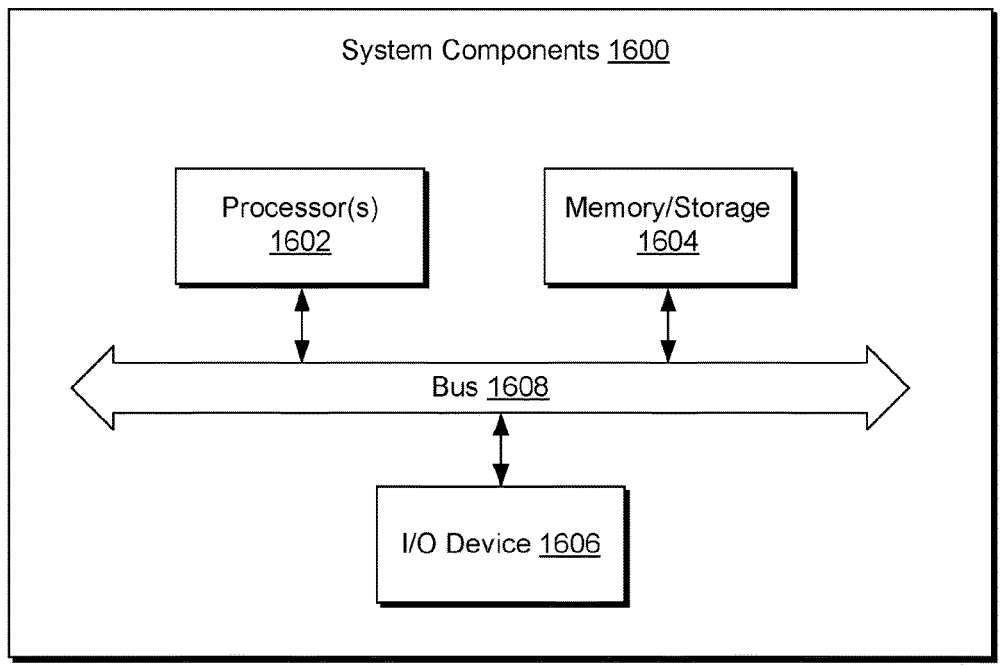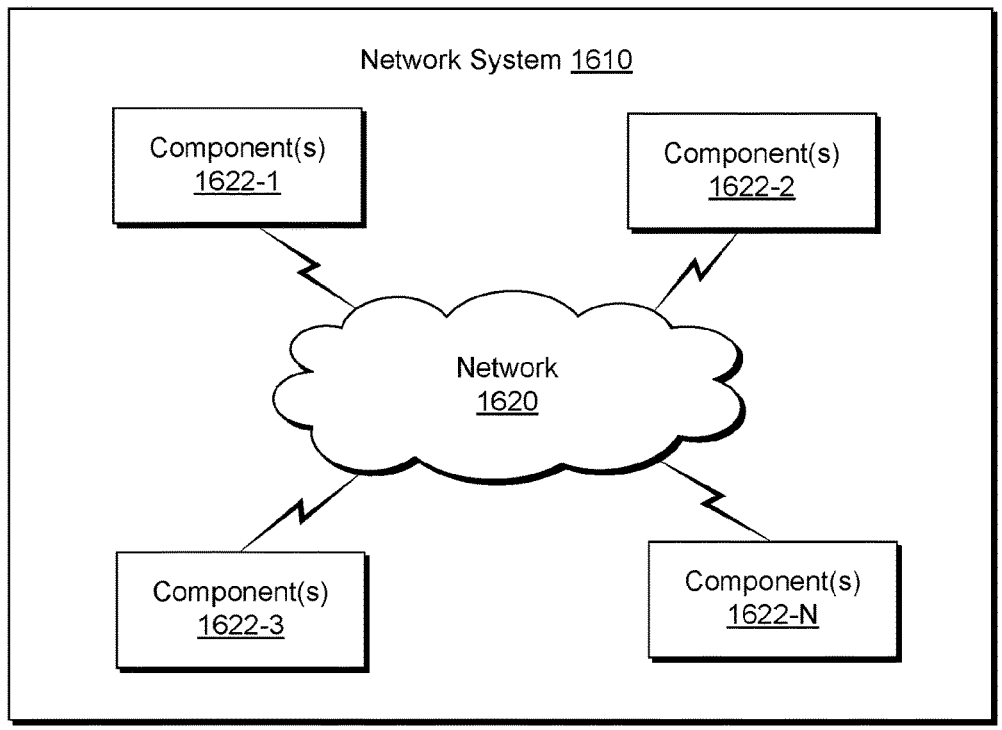
Fig. 16

POROSIMETRY TRANSITION REGION ADJUSTMENT

CROSS-REFERENCE TO RELATED APPLICATIONS

This application claims priority to France Patent Application having Serial No. 1551096, which was filed on Feb. 11, 2015 and is incorporated herein by reference in its entirety.

BACKGROUND

Porosimetry may be used to determine one or more quantifiable aspects of a material's porous nature, such as, for example, pore diameter, total pore volume, surface area, bulk density, absolute density, etc. Porosimetry may involve intrusion, extrusion or intrusion and extrusion of fluid. For example, porosimetry can involve intrusion of a non-wetting liquid into a material through the use of a porosimeter. In such an example, pore size may be determined based on pressure readings as the non-wetting liquid is forced into a pore or pores of the material against an opposing force of the liquid's surface tension with respect to the material.

SUMMARY

A method can include receiving porosimetry data for a range of pressures that spans a transition zone defined at least in part by a high-pressure end of a first pressure zone and a low-pressure end of a second pressure zone; detecting at least one artifact in the transition zone; computing accuracy information for the high-pressure end of the first pressure zone and the low-pressure end of the second pressure zone; computing a pressure-volume adjustment based at least in part on the accuracy information; and outputting a pressure-volume relationship in the transition zone based at least in part on the pressure-volume adjustment. A system can include a processor; memory accessible by the processor; modules stored in the memory that include processor-executable instructions that instruct the system to receive porosimetry data for a range of pressures that spans a transition zone defined at least in part by a high-pressure end of a first pressure zone and a low-pressure end of a second pressure zone; detect at least one artifact in the transition zone; compute accuracy information for the high-pressure end of the first pressure zone and the low-pressure end of the second pressure zone; compute a pressure-volume adjustment based at least in part on the accuracy information; and output a pressure-volume relationship in the transition zone based at least in part on the pressure-volume adjustment. Various other apparatuses, systems, methods, etc., are also disclosed.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Features and advantages of the described implementations can be more readily understood by reference to the following description taken in conjunction with the accompanying drawings.

FIG. 2 illustrates an example of a system and an example of an intrusion process;

FIG. 3 illustrates an example of a method and an example of a system;

FIG. 4 illustrates an example of a graphical user interface (GUI) that may be associated with an analysis framework;

FIG. 16 illustrates example components of a system and a networked system.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

As an example, porosimetry may be applied to a rock core sample such as, for example, a portion of a rock core sample. A rock core sample may be a cylindrical sample of rock acquired using a core bit in conjunction with a core barrel and core catcher. In such an example, the core bit includes cutting structures (e.g., polycrystalline diamond compact (PDC), natural diamond, etc.) about a central hole. The core bit can be rotated to drill around a central cylinder of rock as a rock core sample, which is taken in through the central hole of the bit and into the core barrel. The core barrel serves as a storage chamber for holding the rock core sample while a core catcher can serve to grip the bottom of the rock core sample and, as tension is applied to a drill string, the rock under the rock core sample can be broken away from an undrilled portion of formation below the rock core sample. The core catcher may also act to retain a rock core sample, for example, so that it does not fall out the bottom of the drill string. As an example, porosimetry may be applied to a piece of rock, which may be a rock fragment, for example, from drill cuttings, drill carvings, rock outcrop fragments, etc. As an example, a rock core sample may be regular in shape (e.g., by cutting, etc.), irregular in shape, regular and irregular in shape, etc.

Figure 1:
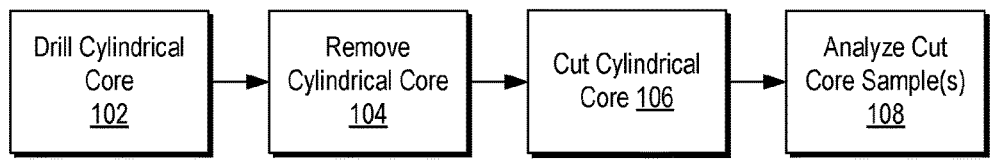
FIG. 1 illustrates an example of a process along with graphical representations of a core and core samples.

FIG. 1 shows an example of a process 100 along with graphical representations of a core 120 from a subsurface formation 101. The process includes cutting a cylindrical core 102; removing the cylindrical core 104; cutting (e.g., "slabbing" or "plugging") the cylindrical core 106, for example, to provide a core slab sample (see, e.g., the slab sample 130) and/or one or more core plug samples (see, e.g., the plug sample 140); and analyzing the one or more samples 108. As illustrated, a cut parallel to the longitudinal axis can expose a planar surface of the core 120 to provide the slab sample 130, which may then be analyzed (e.g., as to layers, lithology, etc.). As illustrated, a cut into a surface of the core 120 can provide the plug sample 140, which may be within a layer to provide an analysis of a particular layer. As an example, where a core includes a large inclination of the bedding plane, the core plug may be taken in a direction parallel to the bedding plane (e.g., to estimate horizontal and vertical permeability). While slab type and plug type samples are illustrated in FIG. 1, samples may be taken in one or more other angles in relation to a bedding plane (e.g., parallel, perpendicular, 45°, etc.) or manners (e.g., by cutting, etc.).

As an example, a core sample may be analyzed to determine petrophysical data. For example, analyses of a core sample may provide measurements of porosity, grain density, horizontal permeability, fluid saturation, etc. As an example, a lithologic description may be made as to one or more portions of the core sample. As an example, analyses may provide for a core gamma log and measurements of vertical permeability. As an example, measurements may be made at various pressure-temperature conditions, including room and/or formation temperature, atmospheric and/or formation confining pressure, etc. Analyses may include routine core analysis (RCA) and/or special core analysis (SCAL). As an example, one or more core analyses may be performed as described in the American Petroleum Institute (API) document "Recommended Practices for Core Analysis" (API RP 40).

Core rock properties provided by logs and sampling can help in reservoir characterization. For example, analyses may determine various reservoir properties of rock. For example, pore aperture, as well as pore throat size and volume distributions, may be obtained by capillary pressure measurements. Techniques for capillary pressure measurements include, for example, the centrifuge method, the porous plate method and the mercury porosimetry, including, but not limited to, mercury injection capillary pressure measurement (MICP) and high-pressure mercury injection (HPMI).

While rock pieces are mentioned, a mercury porosimeter or mercury porosimetry equipment may be used to characterize a variety of porous materials (e.g., ceramics, glasses, catalysts, etc.) via techniques based on capillary phenomena (e.g., liquid penetration into and/or expulsion from pores). In the case of a non-wetting liquid like mercury and an assumption of cylindrical pores, the Washburn equation may be expressed as follows:

$$D = -(1/P) 4\gamma \cos \varphi \quad \text{Eqn. (1)}$$

where D is pore diameter, P is applied pressure, $\gamma$ is surface tension, and $\varphi$ is contact angle. Accordingly, volume of mercury V penetrating pores of a sample may be measured directly as a function of applied pressure P. Such P-V information (e.g., V(P)) can serve to characterize pore structure of a sample (e.g., consider a pressure-volume curve or curves).

FIG. 2 shows an example of a system 210, which may be part of a mercury porosimeter system (e.g., consider a MICROMERITICS AUTOPORE™ mercury porosimeter system, Micromeritics, Norcross, Ga.). As shown, the system 210 includes a penetrometer 215 that can accommodate a rock sample 220 in contact with mercury 222 within a sealable sample cup 224, which is shown as including a cap 226 and an electrical contact 228. The penetrometer 215 also includes a capillary tube stem 230 that is plated with metal plating 232 (e.g., as an electrical contact material for electrical contact 233) and that includes an opening 231 at an end distal to the sealable sample cup 224 where the opening 231 is to a lumen of the capillary tube stem 230 that is in fluid communication with the sealable sample cup 224.

In the example of FIG. 2, the system 210 includes pressure equipment 240 and acquisition equipment 250. As shown, the pressure equipment 240 includes multiple pressure ports (e.g., Port 1, Port 2, . . . , Port N). Such ports may be operatively coupled to the penetrometer 215 to be in fluid communication with the lumen of the capillary tube stem 230 (e.g., to apply pressure to the chamber formed within the sealable sample cup 224).

In the example of FIG. 2, the acquisition equipment 250 can include interfaces that can be electrically coupled to the electrical contact 228 and the metal plating 232, as well as, for example, one or more other interfaces (e.g., for pressure information, pressure control, etc.). As an example, the acquisition equipment 250 may issue instructions to the pressure equipment 240 for pressure to be applied to the lumen of the capillary tube stem 230 via one or more of the ports to pressurize the mercury 222 and drive at a portion of the mercury 222 into pores of the sample 220. As the pores fill, the length of the mercury 222 column in the lumen can change, which, in turn, may be measured electrically via the metal plating 232 (e.g., capacitatively, etc.) as the mercury 222 itself is electrically conductive.

FIG. 2 also illustrates an intrusion process 260 where the sample 220 includes a pore that receives a portion of the mercury 222 under pressure symbolized by masses M1 and M2 as disposed on a plunger. As shown, the mass M2 is greater than the mass M1 and hence more of the mercury 222 has intruded the pore of the sample for mass M2 compared to mass M1.

A system for capillary pressure measurement may provide, as output, one or more capillary pressure curves, for example, constructed using a wetting phase along one axis (e.g., X-axis) and capillary pressure along another axis (e.g., Y-axis). As an example, a capillary pressure curve may be displayed using a petrophysical analysis framework. For example, consider the TECHLOG™ framework (Schlumberger Limited, Houston, Tex.), which can import data, analyze data, export data, etc. Such a framework can include modules with instructions executable by one or more processors to perform computational operations. As an example, consider a cross-plot module that can be executed to cross-plot data and, for example, call for rendering of information (e.g., a cross-plot) to a display, to a printed medium, etc.

As an example, a porosimeter may operate in pressure range from about 0 psia to about 60,000 psia (e.g., from about 0 MPa to about 414 MPa) in a process that can acquire data for pore diameters in a range from greater than about 900 µm to about 0.003 µm. In an effort to deliver precise and reliable measurements in such a pressure (e.g., pore diameter) range, a mercury porosimeter can be equipped with at least two pressure chambers or ports (e.g., each equipped with a dedicated pressure gauge), for example, each for a particular pressure range or pressure zone.

Where equipment includes multiple pressure zones, capillary pressure curves generated by equipment (e.g., mercury porosimetry equipment) can include one or more transition regions. For example, a transition region may exist across a range of pressures that include low-pressure zone and a high-pressure zone. As an example, a low-high-pressure cell transition artifact may exist as caused by transferring a sample from one chamber to another chamber. For example, mercury porosimetry equipment can include multiple chambers, one of which may be a low-pressure chamber and another of which may be a high-pressure chamber where a process involves physically moving a sample (e.g., in a penetrometer) after acquiring data for the low-pressure chamber to acquire data for the high-pressure chamber.

In operation, mercury porosimetry measurement can include partially filling a sample with mercury in a low-pressure chamber by increasing the mercury pressure (e.g., incrementally, etc.) from near-zero until a pressure near to atmospheric conditions is reached. Once the near-atmospheric pressure is reached, the sample may be removed from the low-pressure chamber and transferred to a high-pressure chamber, for example, to cause further mercury injection at higher pressure, well-above atmospheric conditions (e.g., to about 60,000 psi). Data acquired via such a measurement process may be analyzed to characterize the sample, for example, as to pore structure, etc.

FIG. 3 shows an example of a method 300 that includes a reception block 310 for receiving data that includes transition region data, a definition block 320 for defining transition region data, a normalization block 330 for normalizing at least a portion of the data (e.g., and/or applying one or more other techniques), and an output block 340 for outputting transition region information.

As an example, in the method 300, the reception block 310 may include receiving porosimetry data for a range of pressures that spans a transition zone defined at least in part by a high-pressure end of a first pressure zone and a low-pressure end of a second pressure zone; the definition block 320 may include defining the transition zone, which may include detecting at least one artifact (e.g., as associated with a transition between pressure zones); the normalization block 330 may include a computation block for computing accuracy information for the high-pressure end of a first pressure zone and the low-pressure end of a second pressure zone and a computation block for computing a pressure-volume adjustment based at least in part on the accuracy information; and the output block 340 may include outputting transition region information that includes a pressure-volume relationship in the transition zone based at least in part on the pressure-volume adjustment.

The method 300 is shown in FIG. 3 in association with various computer-readable media (CRM) blocks 311, 321, 331 and 341. Such blocks generally include instructions suitable for execution by one or more processors (or cores) to instruct a computing device or system to perform one or more actions. While various blocks are shown, a single medium may be configured with instructions to allow for, at least in part, performance of various actions of the method 300. As an example, a computer-readable medium (CRM) may be a computer-readable storage medium that is non-transitory and not a carrier wave.

FIG. 3 also shows an example of a system 350 that includes one or more information storage devices 352, one or more computers 354, one or more networks 360 and one or more modules 370. As to the one or more computers 354, each computer may include one or more processors (e.g., or processing cores) 356 and memory 358 for storing instructions (e.g., modules), for example, executable by at least one of the one or more processors. As an example, a computer may include one or more network interfaces (e.g., wired or wireless), one or more graphics cards, a display interface (e.g., wired or wireless), etc.

As an example, the one or more modules 370 may include instructions (e.g., stored in memory) executable by one or more processors to instruct the system 350 to perform various actions (e.g., consider one or more of the computer-readable media (CRM) blocks 311, 321, 331 and 341). As an example, the system 350 may be configured such that the one or more modules 370 provide for establishing a framework or a portion thereof. As an example, one or more methods, techniques, etc. may be performed using one or more modules, which may be, for example, one or more of the one or more modules 370 of FIG. 3.

As an example, porosimetry may involve applying pressure over one or more pressure zones. For example, a porosimeter may apply pressure over a first zone to force liquid into a porous sample and then apply pressure over a second zone to force additional liquid into the porous sample. In such an example, a transition region may exist for the first zone and the second zone. As an example, a method such as, the method 300, may act to bridge a first pressure zone data and second pressure zone data across a transition region. Such a method may act to reduce the impact of one or more artifacts that may result at least in part from transferring a sample from one chamber to another chamber (e.g., from a first pressure zone chamber to a second pressure zone chamber, from a second pressure zone chamber to a third pressure zone chamber, etc.).

As an example, the method 300 may include defining artifact points as being associated with a transition region. For example, highest-pressure point(s) acquired by a lower pressure gauge and lowest-pressure points acquired by a higher pressure gauge may be defined to be artifact points and considered to be transition region data. As an example, normalization may be applied in a manner that acts to mitigate one or more artifacts, for example, via smoothing, removing points, recalculating slopes, etc. As an example, a method may output transition region information that can increase capillary pressure curve compatibility with capillary pressure models (e.g., mathematical models, etc.).

FIG. 4 shows an example of a graphical user interface (GUI) 410 that may be part of a framework executed using one or more processors, memory accessibly the at least one of the one or more processors, etc. As an example, the GUI 410 may be part of a framework such as the TECHLOG™ framework. As an example, the GUI 410 may be used to implement a workflow that includes analyzing capillary pressure data. For example, a user may navigate the GUI 410 to select a capillary pressure module as indicated by a capillary pressure graphical control 420, which may cause rendering of menu options that includes a pressure transition artifact reduction graphical control 440 that can implement a pressure transition artifact reduction module. As an example, a pressure transition artifact reduction module may include instructions stored in memory accessible by at least one processor where execution of the instructions may implement at least a portion of the method 300 of FIG. 3.

As shown in FIG. 4, the GUI 410 may include various options associated with core analysis, which, in turn, may aid in characterizing rock such as reservoir rock (e.g., hydrocarbon reservoir rock, etc.). As an example, a workflow may include one or more worksteps associated with one or more graphical controls of the GUI 410. As an example, a workflow may include one or more worksteps associated with the process 100 of FIG. 1. As an example, a workflow may include performing one or more field operations, for example, in a field from which a rock sample was extracted. As an example, a field operation may include acquiring one or more samples, drilling, injecting fluid, producing fluid, etc. As an example, a field operation may depend in part on results of an analysis of a sample of rock or samples of rock.

As mentioned, mercury porosimetry can include subjecting a sample to multiple pressure zones. As an example, an analysis can include loading a porous sample into a penetrometer (see, e.g., the penetrometer 215 of FIG. 2). Once loaded, the penetrometer may be installed in a low-pressure port of a porosimeter (see, e.g., pressure equipment 240 of FIG. 2). In such an example, a first phase of low-pressure analysis can include evacuation of gases from the penetrometer. The penetrometer may then be backfilled (e.g., automatically) with mercury. In a second phase of the low-pressure analysis, data may be collected at pressures up to a last low-pressure point as may be specified in a previously defined pressure table (see, e.g., the acquisition equipment 250 of FIG. 2). When the low-pressure analysis is complete, the penetrometer may be removed from the low-pressure port and installed in a high-pressure port. Before penetrometer transfer from the low-pressure chamber to the high-pressure chamber, the low-pressure port may be returned to near atmospheric pressure, so during handling, the penetrometer is in contact with atmospheric conditions. Continuing with high-pressure analysis, data may be collected at pressures indicated in a high-pressure portion of a pressure table.

Pore volume data acquired during a measurement process may be processed in a manner that determines the volume of mercury remaining in the penetrometer stem. For example, as pressure increases, mercury moves into the sample's pores, vacating the stem (e.g., in an intrusion process). According to the Washburn equation, intrusion of different size pores occurs at different pressures. Because mercury has a high surface tension and is non-wetting to various materials, its angle of contact and radius of curvature may be used to calculate pore diameter into which it intrudes at a given pressure (e.g. according to the Washburn equation).

After completion of analysis in a particular chamber (e.g., port, etc.), the penetrometer may transferred to another, next higher-pressure range chamber, if available. Thus, data may include multiple transition zones. Various examples described below consider operation of a mercury porosimeter as to multiple chambers, illustrated with reference to a low-pressure zone (e.g., or chamber or port) and a high-pressure zone (e.g., or chamber or port).

As mentioned, volume of mercury in a penetrometer's stem may be measured, for example, by determining the penetrometer's electrical capacitance. Capacitance is the amount of electrical charge stored per volt of electricity applied. The penetrometer's capacitance varies with the length of penetrometer stem that is filled with mercury, which is electrically conductive.

When a penetrometer is initially backfilled with mercury, the mercury may extend an entire length of the penetrometer. As increasing pressure causes the mercury to intrude into the sample's pores, the volume of mercury in the penetrometer stem decreases by an amount equal to the volume of the pores filled. This decrease in the length of the penetrometer stem that is filled with mercury causes a reduction in the penetrometer's capacitance. Equipment may convert measurements of a penetrometer's capacitance into data points, for example, showing the volume of mercury intruding into the sample's pores. Such equipment may include, for example, memory that can store instructions and one or more processors that can execute such instructions (e.g., to receive data, process data, output data, etc.).

As an example, data may be presented as a measured curve V(P), where V is mercury saturation of a porous sample and P is applied mercury pressure. Such a curve may be referred to as capillary curve and it may serve to characterize pore structure as it holds information about pore interconnections, pore size and volume distributions, etc.

Figure 5:
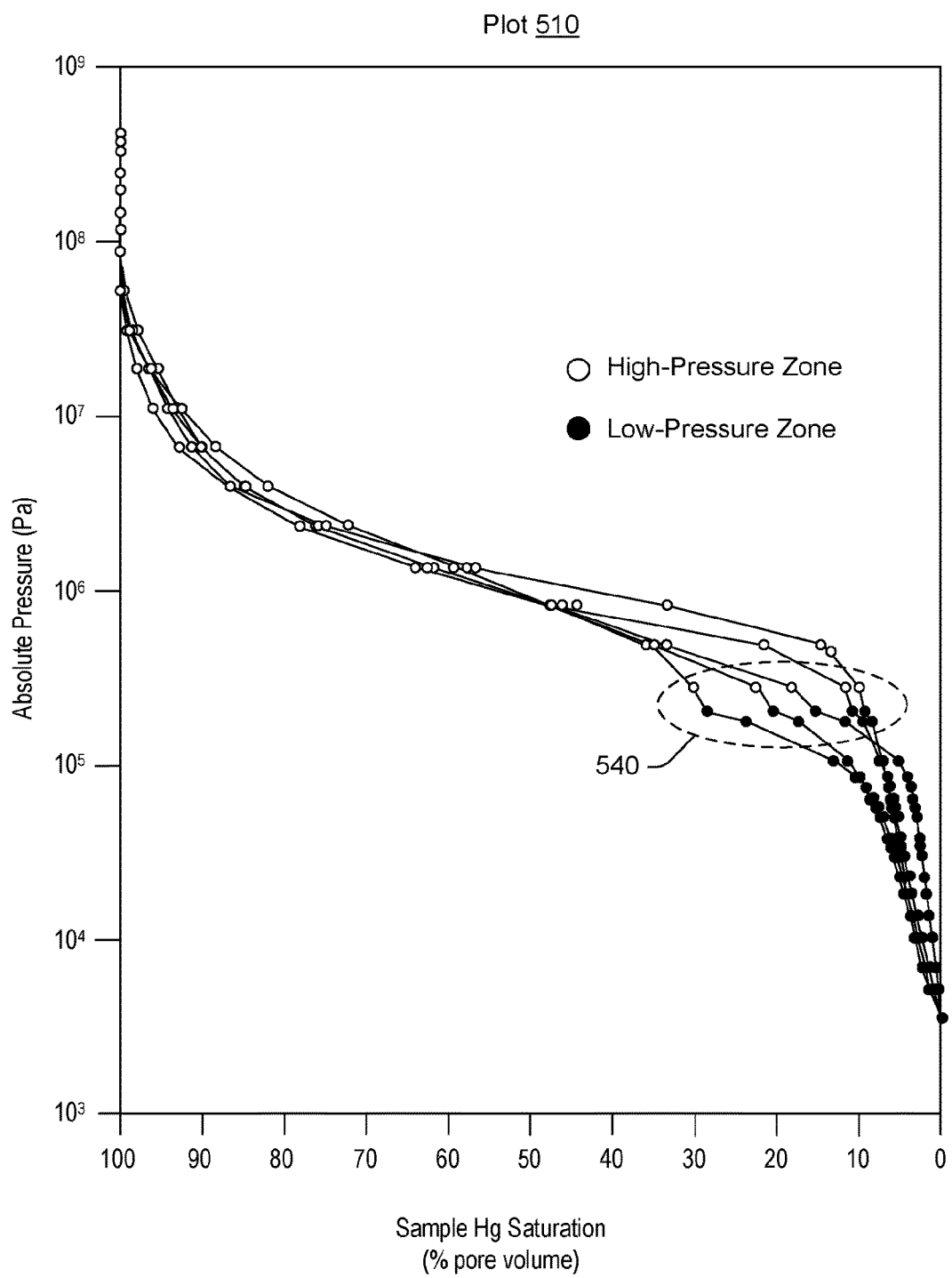
FIG. 5 illustrates an example of a plot.

FIG. 5 shows an example of a plot 510 of pressure versus Hg saturation. As an example, a capillary pressure curve obtained using mercury porosimetry may include a transition artifact(s) between low-pressure chamber and high-pressure chamber data. In FIG. 5, a transition region 540 is identified that illustrates various transition artifacts (e.g., bumps, breaking slopes, etc.). As an example, there may be a relatively consistent appearance of a sharp transition for different porous samples, however, where artifacts exist over a common pressure range span, such artifacts are not likely indicative of pore space structure but rather indicative of artifacts of a measurement process.

As to reasons for artifacts within a transition zone, consider one or more of the following: (a) jerks of operator handling mercury-filled penetrometer, while it is being transferred from a low-pressure to a high-pressure chamber (e.g., port, etc.) where such abrupt movement(s) may lead to non-observable (e.g., spurious) mercury intrusion between a last measurement in a low-pressure chamber and a first measurement in high-pressure chamber; and (b) mismatch or a sharp contrast between pressure measuring accuracies in low-pressure and high-pressure chambers.

As to abrupt movements as a reason, training and care in handling may act to reduce their impact on data while, as to the measuring accuracy contrast, it may be hardware-related and remain even if an experiment is conducted with minimal human factors or without human factors.

Knowledge of measuring accuracy in mercury porosimetry proves helpful during experiment planning, controlling of quality, as well as processing and interpreting experimental data. To estimate uncertainties of P and V measurements, a method can include receiving one or more parameters of accuracy, for example, consider confidence interval, shape of error statistical distribution and repeatability factor.

As an example, assume a measured value P has an absolute error $\Delta P$ in relation to true value $P_{true}$, and so does a value V:

$$(P-\Delta P) \leq P_{true} \leq (P+\Delta P); \Delta P \geq 0$$

$$(V-\Delta V) \leq V_{true} \leq (V+\Delta V); \Delta V \geq 0 \qquad \text{Eqn. (2)}$$

As an example, relative errors (inverse to accuracies) $\delta P$ and $\delta V$ can be defined as follows:

$$\delta P = \Delta P/P; \delta P > 0$$

$$\delta V = \Delta V/V; \delta V > 0 \qquad \text{Eqn. (3)}$$

Table 1, below, shows some examples of technical specifications of porosimeters.

TABLE 1

Examples of Porosimeter Information

|  | Porosimeter Example A | Porosimeter Example B |
|---|---|---|
| Low pressure: | | |
| Measurement: | 0-50 psia (345 kPa) | 0-50 psia (345 kPa) |
| Resolution: | 0.01 psi (69 Pa) | 0.01 psi (69 Pa) |

TABLE 1-continued

Examples of Porosimeter Information

| | Porosimeter Example A | Porosimeter Example B |
|---|---|---|
| Pore Diameter: | 360-3.6 μm | 900 (or more)-3.6 μm |
| Transducer Accuracy: | no information | ±1% of full scale (transducer manufacturer's specifications) |
| High pressure: | | |
| Measurement: | From atmospheric pressure to 60,000 psia (414 MPa) | From atmospheric pressure to 60,000 psia (414 MPa) |
| Resolution: | 0.3 psi (2,070 Pa) for pressure range 5-60 kpsia (34-414 MPa) 0.03 psi (207 Pa) from atmospheric pressure to 5 kpsia (34 MPa) | 0.3 psi (2,070 Pa) for pressure range 5-60 kpsia (34-414 MPa) 0.1 psi (689 Pa) from atmospheric pressure to 5 kpsia (34 MPa) |
| Pore Diameter: | 6-0.003 μm | 6-0.003 μm |
| Transducer Accuracy: | ±1% of full scale (transducer manufacturer's specifications) | ±0.1% of full scale (transducer manufacturer's specifications) |
| Intrusion: | | |
| Resolution: | Better than 0.1 μL | Better than 0.1 μL |
| Accuracy: | ±1% of maximum penetrometer stem volume | ±1% of maximum penetrometer stem volume |
| Penetrometers: | | |
| Possible Volumes of Capillary Stem: | 0.38; 1.1; 1.7; 3.1 and 3.9 cm$^3$ | 0.38; 1.1; 1.7; 3.1 and 3.9 cm$^3$ |
| Maximum Sample Dimensions: | Cylinder Ø2.5 cm with length 2.5 cm | Cylinder Ø2.5 cm with length 2.5 cm |

Porosimeter technical specifications (see, e.g., examples of Table 1) indicate that accuracies of pressure transducers may be given as absolute values that correspond to a certain percentage of full scale. In turn, this implies maximum relative accuracy in upper part of scale (high-pressure values) and minimal relative accuracy in lower part of the scale (low-pressure values). In addition, pressure measurement ranges of low-pressure and high-pressure ports can overlap each other. The latter circumstance may allow, for example, an operator transferring a penetrometer with a probed sample inside from low-pressure chamber to high-pressure chamber without reaching maximal possible pressure and hence maximal accuracy in low-pressure port.

For a mercury porosimeter with characteristics such as the Example Porosimeter B specified in Table 1, the following expressions for relative errors of P and V measurements may be used:

$$\delta P = \Delta P/P; \Delta P = 3.45 \text{ kPa if } P \text{ falls within the range } 0 \text{ to } 345 \text{ kPa}$$

$$\delta P = \Delta P/P; \Delta P = 414 \text{ kPa if } P \text{ falls within the range } 0 \text{ to } 414 \text{ MPa} \quad \text{Eqn. (4)}$$

$$\delta V = \Delta V/V; \Delta V = 1\% \text{ of capillary stem volume} \quad \text{Eqn. (5)}$$

From Eqn. (4), a sharp contrast between pressure measuring accuracies in low-pressure and high-pressure chambers may be taken into account. As an example, a method may include using Eqns. (3) and (4) and plotting information graphically, for example, for a particular version or generation or design of mercury porosimeter.

Figure 6:
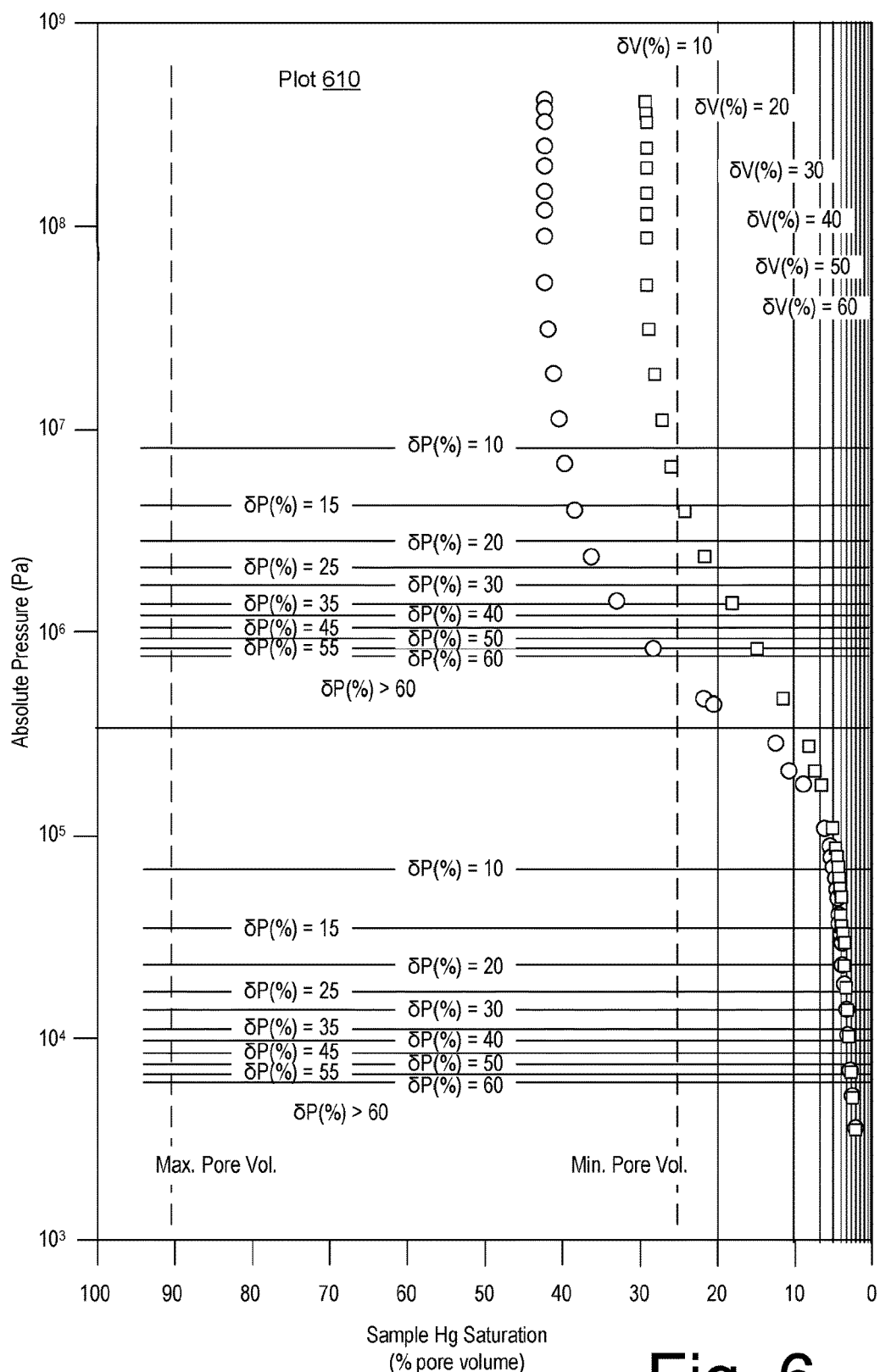
FIG. 6 illustrates an example of a plot.

FIG. 6 shows an example plot 610 where information as in Eqns. (3) and (4) is represented graphically. As an example, a GUI such as the GUI 410 of FIG. 4 may include a graphical control that may be selected (e.g., actuated) to select a type of mercury porosimeter and to present a plot such as the plot 610. As an example, a framework may include a data storage or an interface that can access a data storage that includes information such as information of the plot 610 or, for example, information as in one or more of Eqns. (3) and (4).

As an example, an accuracy diagnostic plot (e.g., or information) may be utilized to estimate quality of one or more V(P) curves and/or, for example, to screen data points of acceptable accuracy and/or quality. An inspection of plot may help to explain one or more root causes of an artifact, for example, relatively low accuracy of pressure reading in high-pressure chamber if the penetrometer is transferred from a low-pressure to a high-pressure chamber, but maximal pressure and, thus, maximal accuracy in low-pressure chamber was not reached (see, e.g., the plot 510 of FIG. 5).

Ignorance of an artifact may lead to an erroneous mercury porosimetry data interpretation and, for example, conclusions about pore space structure of the studied samples that may be lacking. For example, consider possible negative consequences such as wrong pore size of pore volume distributions, non-accurate calculation of porosity, permeability, phase permeability, sample saturation, threshold pressures, etc.

As an example, a method may include determining one or more artifact points and making one or more adjustments that can reduce error due to a transition between two pressure zones (e.g., a low-pressure zone and a high-pressure zone) of one or more mercury porosimetry capillary pressure curves. As an example, a method may include using capillary pressure measurements from multiple systems (e.g., different pieces of mercury porosimetry equipment, different types of mercury porosimetry equipment, etc.).

As an example, a method can include scanning capillary pressure curve data and identifying an artifact in a particular range of capillary pressure, for example, where the artifact corresponds to a system's transition limit constraint(s). As an example, a method may include receiving user input as to a user-selected pick, for example, as an option where an automated procedure may fail to identify one or more artifact points. As an example, a method may determine what type of adjustment(s) to make based at least in part on one or more accuracy boundaries, for example, as may be set up by a system used to make measurements.

As an example, a workflow may allow a user to optimize information provided by one or more capillary pressure curves, for example, in a manner that includes taking into account uncertainty of measurements. Such an approach may facilitate modeling of data (e.g., as to one or more samples), for example, using one or more capillary pressure models.

Figure 7:
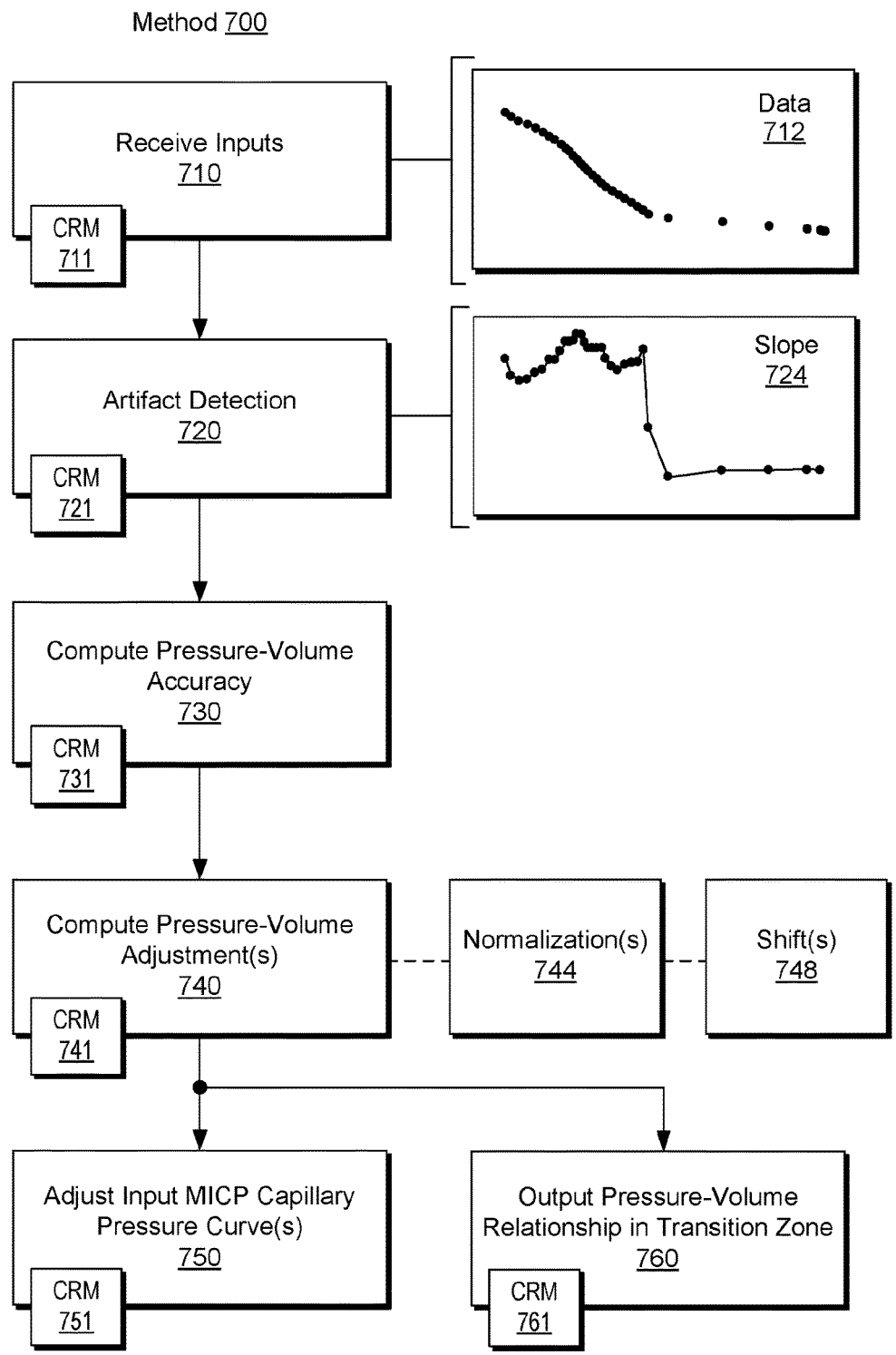
FIG. 7 illustrates an example of a method.

FIG. 7 shows an example of a method 700 that may be optionally implemented as a workflow, as part of a workflow, etc. As shown, the method 700 includes a reception block 710 for receiving inputs (e.g., specifying inputs, etc.), a detection block 720 for detecting one or more artifacts, a computation block 730 for computing pressure-volume accuracy, a computation block 740 for computing one or more pressure-volume adjustments, and an adjustment block 750 for adjusting capillary pressure information (e.g., adjusting information as to one or more capillary pressure curves) and/or an output block 760 for outputting an adjusted pressure-volume, for example, at least in part in a transition zone (e.g., a zone that spans two pressure zones).

The method 700 is shown in FIG. 7 in association with various computer-readable media (CRM) blocks 711, 721, 731, 741, 751 and 761. Such blocks generally include instructions suitable for execution by one or more processors (or cores) to instruct a computing device or system to perform one or more actions. For example, consider the system 350 of FIG. 3 where the modules 370 may include one or more of the CRM blocks 711, 721, 731, 741, 751 and 761. While various blocks are shown, a single medium may be configured with instructions to allow for, at least in part, performance of various actions of the method 700. As an example, a computer-readable medium (CRM) may be a computer-readable storage medium that is non-transitory and not a carrier wave.

As to the reception block 710, a user may input wetting phase data and mercury porosimetry capillary pressure curve data. For example, the reception block 710 can include receiving porosimetry data for a range of pressures that spans a transition zone (e.g., or transition zones) defined at least in part by a high-pressure end of a first pressure zone and a low-pressure end of a second pressure zone. As an example, a user may specify a type, model, design, etc., of mercury porosimeter utilized to measure the capillary curve and, for example, associated technical specifications (see, e.g., Table 1). As an example, with respect to the reception block 710, the following types of information may be input: (a) accuracy of individual gauges (e.g., in low and high-pressure chambers, etc.); and (b) a search range of a capillary transition zone, for example, according to technical specifications and methodology of a utilized mercury porosimeter. As an example, a condition may be set that an artifact is not to be considered to lie outside a specified range.

As to the detection block 720, one or more techniques may be employed for detection of one or more artifact points. For example, detection may occur automatically, semi-automatically or manually. An automatic or semi-automatic technique may include receiving information and processing the information with respect to one or more statistical techniques. As an example, a semi-automatic technique or a manual technique may include navigating a cursor, touching a touch-sensitive display, etc. to identify a region or regions within which one or more artifact points may exist, as well as individual artifact point(s).

As an example, to detect an artifact automatically, a program may be executable to consider multiple groups of points on a capillary curve (e.g., or curves). Such a program may implement an algorithm that applies one or more methods of detection on one or more groups and that compares results of the one or more methods to select the group (e.g., or groups) that corresponds to an artifact.

As an example, where more than one artifact between the highest-pressure point of capillary pressure curve obtained in low-pressure chamber and lowest-pressure point of capillary pressure curve obtained in high-pressure chamber exists, a program may return an artifact point and, for example, a user may guide the program on its search. Such an approach may be considered to be, at least in part, a manual search for the artifact points because the user enters a pressure-saturation range where the effective artifact is likely to occur. Such an approach may lead an algorithm to detect proper artifact points instead of locating false artifact points.

As an example, a user may know when a transition is complete. In such an example, the user may enter the highest-pressure point of capillary pressure curve obtained in low-pressure chamber and lowest-pressure point of capillary pressure curve obtained in high-pressure chamber.

As an example, one or more algorithms may be employed to perform an artifact search. For example, consider detection by slopes where an algorithm calculates successive slopes or derivatives of P(V) curve and when the middle slope is higher than the external slopes or a user-defined threshold, an artifact is identified. In such an example, the algorithm may take a window of about four points and calculate three slopes. Where the slope in the middle is higher than the slope superior and the slope inferior, the algorithm can recognize an artifact. As an example, a selected number of points may be at least greater than a number of calculated slopes, for example, a method may include calculating one slope (derivative value) using two or more adjacent points where more than two points may act to stabilize derivative values.

As an example, FIG. 7 shows a data plot 712 that may be associated with the reception block 710 and a slope plot 724 that may be associated with the detection block 720, for example, as part of a detection technique to detect one or more artifacts. As an example, a detection algorithm may include calculating derivatives of data and outputting derivative information. As an example, such an algorithm may calculate one or more derivatives over an increment or increments (e.g., a window or windows). As to the plot 712, an equation such as Log (P[i+1]/P[i])/(CSW[i+1]−CSW[i]) may be applied where "i" and "i+1" are indexes that correspond to a data structure (e.g., P and CSW data indexed in memory, etc.). As an example, a Taylor series expansion approach may be implemented to approximate a derivative or derivatives.

Figure 8:
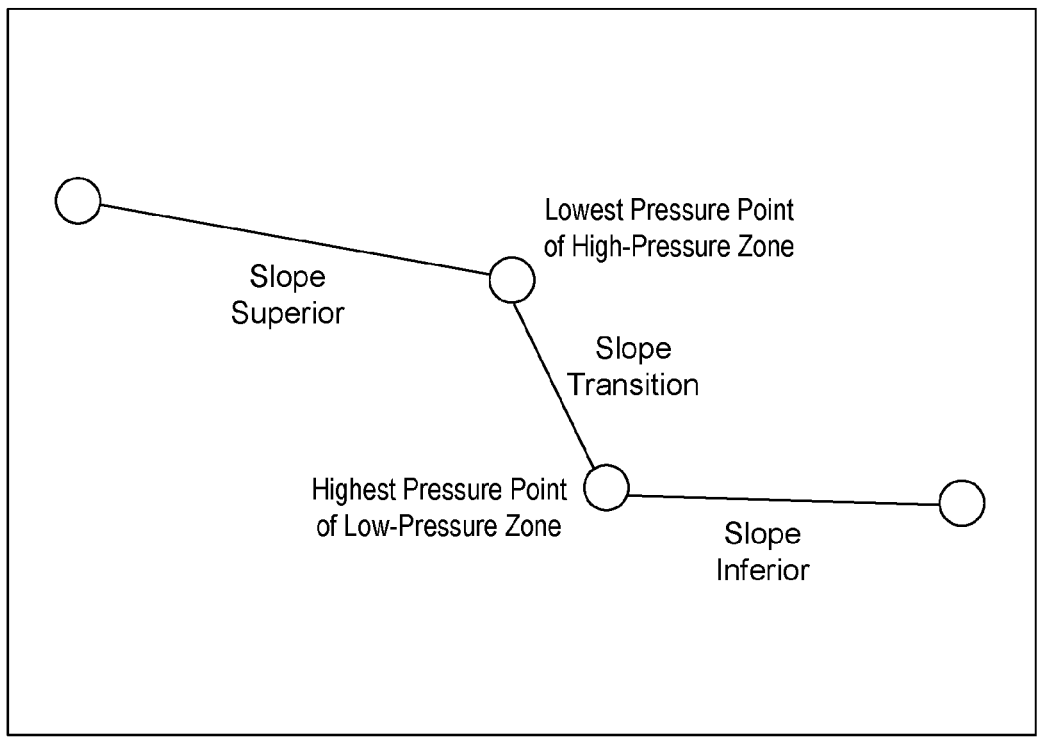
FIG. 8 illustrates an example of a plot.

FIG. 8 shows an example plot 810 where four points may be considered by an algorithm in an effort to identify an artifact point. As shown, three slopes may be determined using the four points: (i) a slope superior, (ii) a slope inferior, and (iii) a slope transition. As shown, the slope transition spans the lowest pressure point of the high-pressure zone and the highest pressure point of the low-pressure zone and it is higher than the slope superior and higher than the slope inferior, which is indicative of an artifact. As an example, slope calculations may be performed using an algorithm or algorithms. As an example, an algorithm or algorithms may be implemented via instructions executable by one or more processors. As an example, one or more algorithms may be used to analyze data as to slope(s), derivative(s), shape, curvature, continuity, discontinuity, etc. to, for example, identify an artifact or artifacts.

As an example, a detection algorithm may include breaking slopes. For example, an algorithm may provide for calculating slopes of two consecutive lines. In such an example, if the difference between the slopes is higher than the bisector, the algorithm can identify an artifact.

As to the computation block 730 of the method 700 of FIG. 7, once one or more artifact points are detected (e.g., identified, found, etc.) per the detection block 720, the pressure and volume accuracy curves may be calculated, for example, for each input mercury porosimetry V(P) curve.

As mentioned, differences can exist in pressure and volume accuracy for two pressure zones (e.g., chambers, ports, etc.). For example, as illustrated in the plot 610 of FIG. 6, differences can exist between a low-pressure chamber and a high-pressure chamber.

For various types of equipment, a relatively large gap of pressure accuracy can exist between the highest-pressure points obtained in the low-pressure chamber and the lowest-pressure points obtained in the high-pressure chamber (see, e.g., Table 1 and FIG. 6).

As an example, artifact points may be classified as follows: (a) high-pressure part of capillary curve from the low-pressure chamber corresponds to the artifact lower limit; or (b) low-pressure part of capillary curve from the high-pressure chamber corresponds to the artifact upper limit. As an example, the plot 510 of FIG. 5 may be considered to include such classified artifact points within the transition zone 540 (see, e.g., open circles and filled circles).

Regarding accuracy of a system, individual chambers (e.g., ports, gauges, etc.) can have their own accuracies as to pressure. As an example, a method can include computing pressure accuracy information for two zones that define a transition zone. For example, pressure accuracy curves may be computed from both sides of an artifact such that four global zones are delimited: two zones of highest Hg pressure accuracy associated with high-pressure parts for both capillary curves from low-pressure and high-pressure chambers; and two zones of the lowest Hg pressure accuracy associated with low-pressure part capillary curves from low-pressure and high-pressure chambers. Such zones provide general trends for pressure measurement accuracy of a mercury porosimeter and they depend on technical specifications of the equipment.

Figure 9:
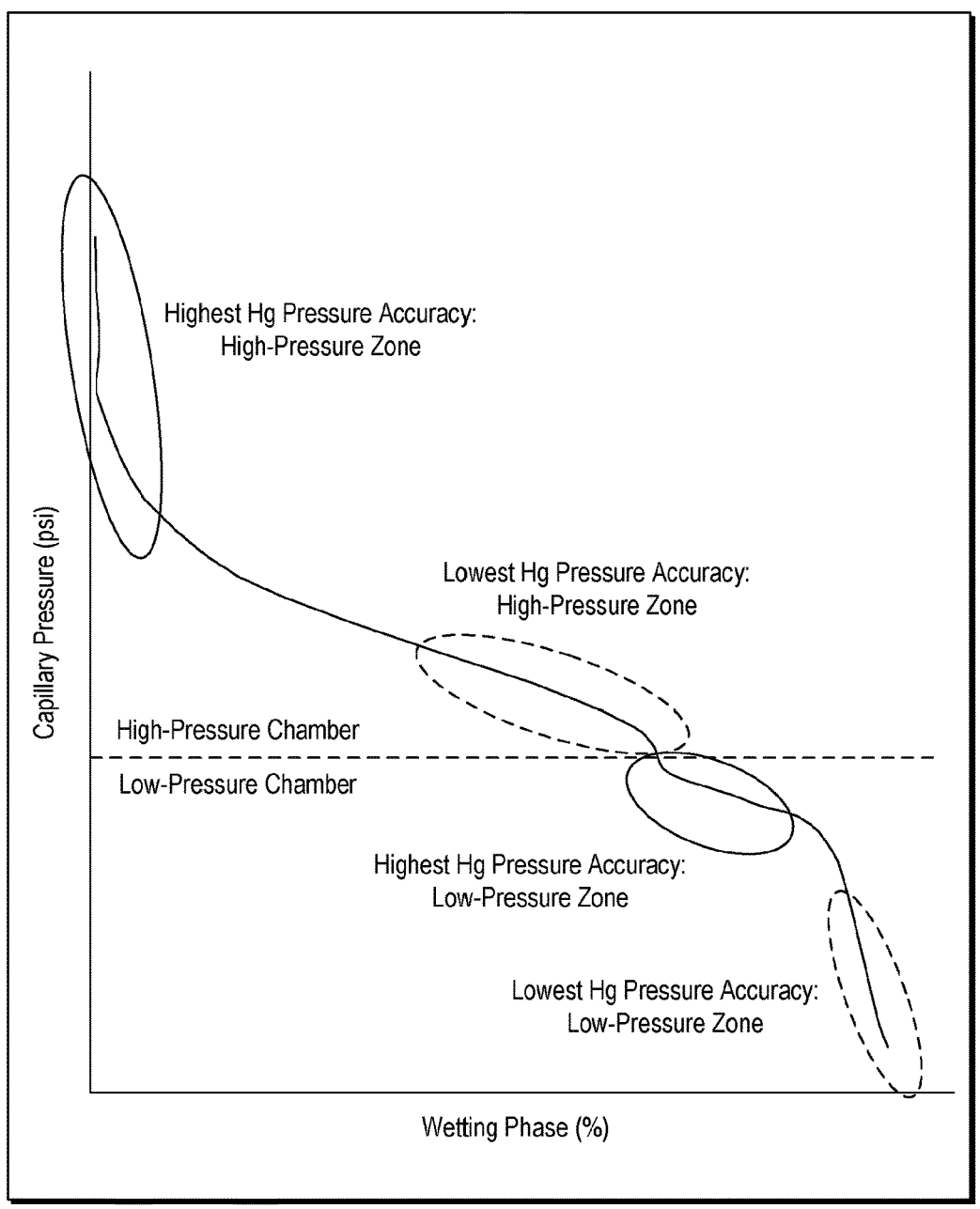
FIG. 9 illustrates an example of a plot.

FIG. 9 shows an example plot 910 that includes various zones. As an example, accuracy curves can give boundaries within which adjustments of data points can be made (e.g., modifications, etc.). As an example, a method can include adjusting data points within defined accuracy boundaries.

As to the computation block 740 of the method 700 of FIG. 7, upon computation of pressure-volume accuracy curves, one or more adjustments may be computed for one or more points of a mercury porosimetry V(P) curve (e.g., within accuracy boundaries that may have been delimitated). As shown in the example of FIG. 7, the computation block 740 may implement one or more normalization techniques 744 and/or one or more shift techniques 748.

Figure 10:
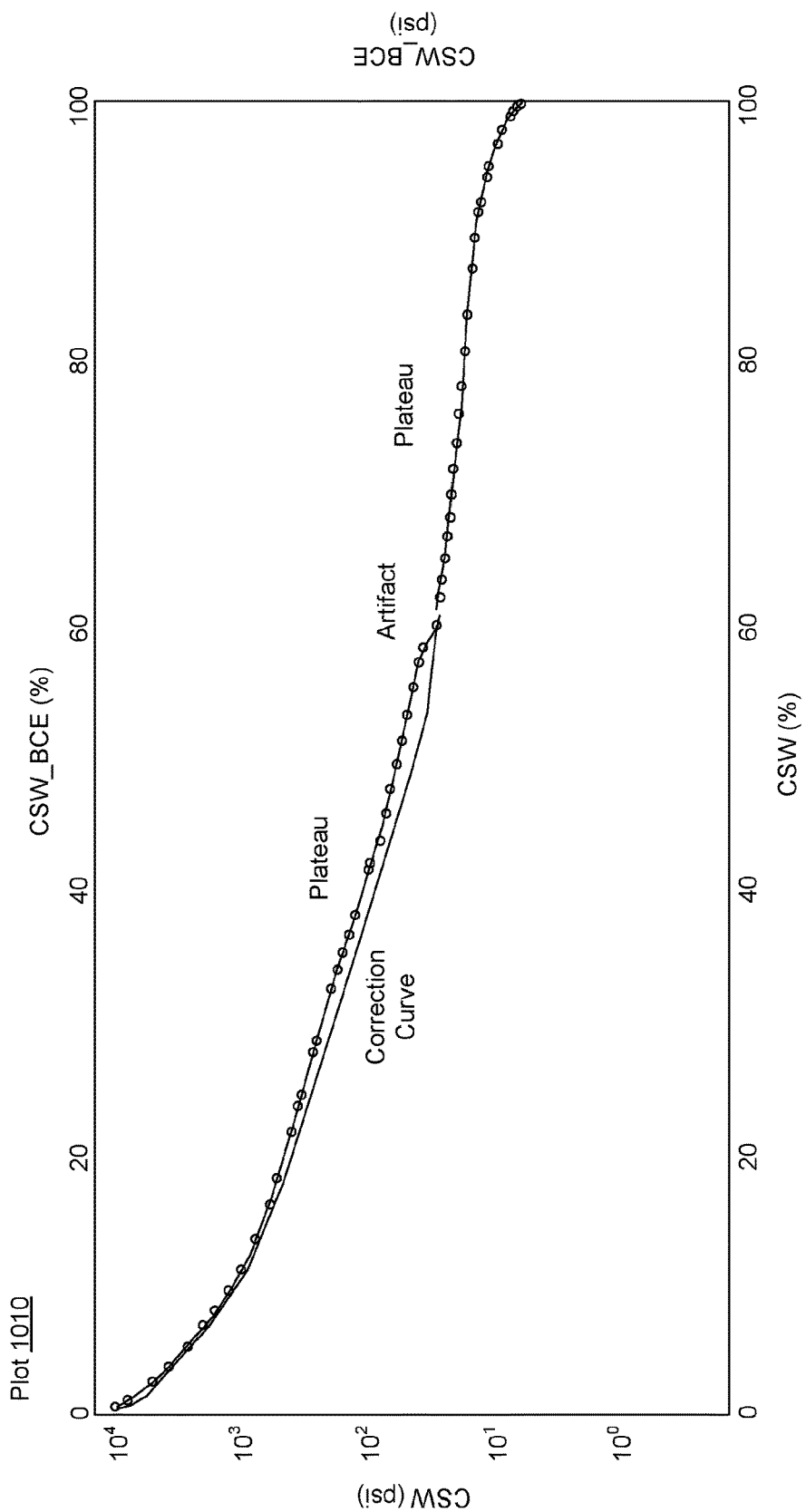
FIG. 10 illustrates an example of a plot.

As an example, a normalization technique may aim to adjust for an artifact on a capillary pressure curve with least discrepancy of pressure. FIG. 10 shows an example plot 1010 where a pressure jump is less than about 10 psi, and an artifact is bound by two plateaus. To level up the curve from the high-pressure chamber to the curve from the low-pressure chamber, a normalization technique may be employed. For example, the lowest pressure point from the high-pressure chamber can be shifted to lower pressure approximately equally to the highest pressure point from the low-pressure chamber. As an example, points from the high-pressure chamber curve can be proportionally shifted as follows: points at the artifact can be shifted by a delta identified (e.g., approximately equal to the pressure jump). As an example, highest pressure from the high-pressure chamber may remain un-shifted and, for example, points between can be shifted using a proportional factor. For instance, consider shifting a mid-way point by about 50 percent of the delta pressure.

As an example, a curve reshaping technique may reshape a curve at a location of an artifact, refining a transition within accuracy boundaries. For example, where an artifact may be characterized more as a breaking slope than a bump, as considered below, on the capillary pressure curve, the curve may be adjusted in a manner that may differ from the aforementioned normalization example. As an example, reshaping of a curve may be made via computing one or more new curves, for example, within accuracy boundaries, and refining the angles of transition between the slopes. As an example, to perform a refinement (e.g., an adjustment), a method may implement an artifact detection technique on a reshaped curve and, if it finds an artifact, the refinement may be improved. In such an example, a loop may exist until a desired level of refinement is reached.

Figure 11:
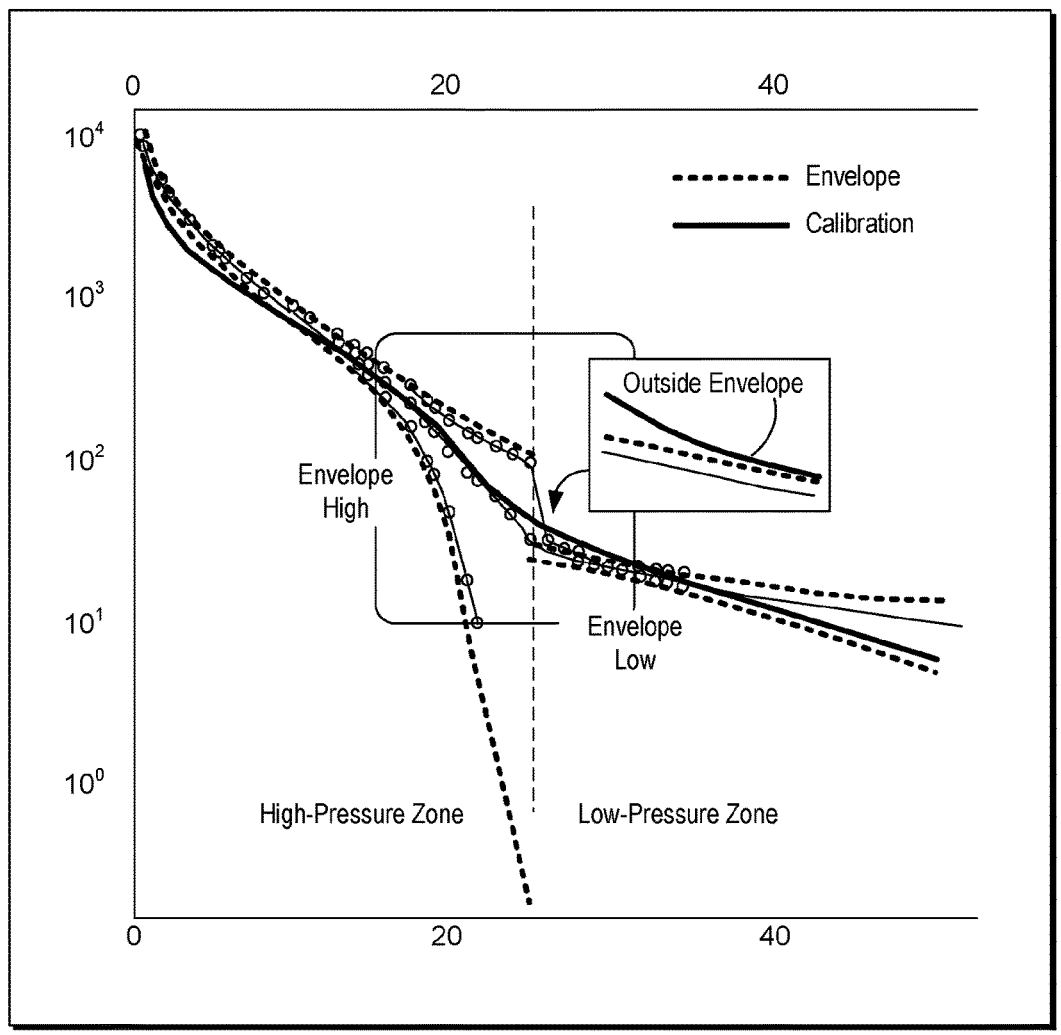
FIG. 11 illustrates an example of a plot.

FIG. 11 shows an example plot 1110 where an adjusted capillary pressure curve has an accepted shape but the curve falls outside of accuracy boundaries, in such an example, an adjust may not be applied.

Figure 12:
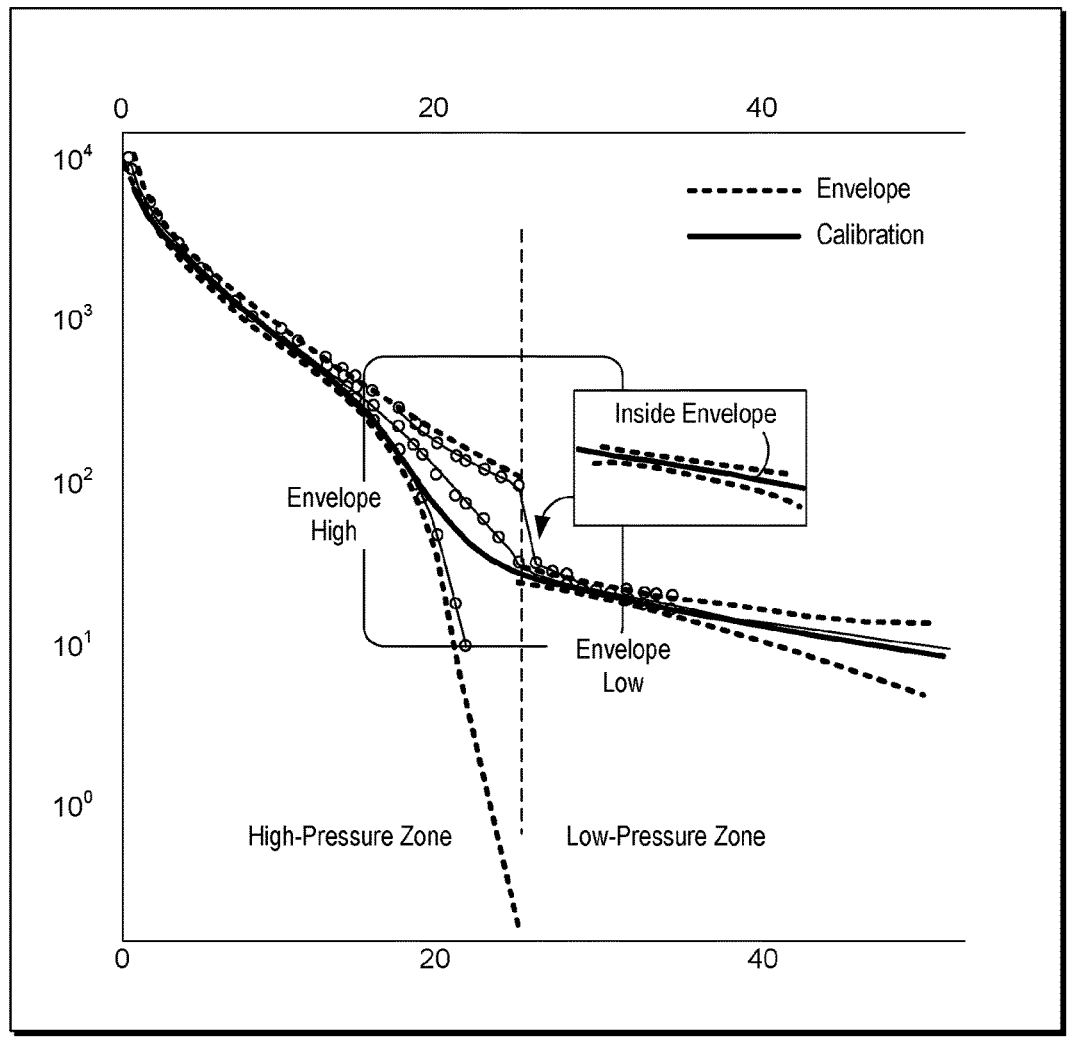
FIG. 12 illustrates an example of a plot.

FIG. 12 shows an example plot 1210 where an adjusted capillary pressure curve has an acceptable shape inside accuracy boundaries. In such an example, the adjustments may be accepted.

As an example, a static shift of high-pressure part and/or low-pressure part of capillary pressure curve along pressure and/or Hg volume coordinates may occur. In such an example, the shapes of both parts may be preserved in their original state and positional relationship adjusted in the pressure–Hg volume domain. Such an approach may aim to reduce discontinuity between a point with a lowest accuracy and a point with a largest accuracy.

As an example, a method may operate as follows: (a) low-pressure cell data remain unmodified; (b) high-pressure cell data are modified near a detected artifact where the highest-pressure part of the high-pressure capillary curve is not modified, for example, in the instance that a reshaping algorithm did not call for such a modification; (c) one or more individual points of an original mercury porosimetry capillary pressure curve can be moved freely along a Hg pressure axis and/or an Hg intrusion volume axis, but within corresponding accuracy boundaries of pressure and intrusion measurement (see, e.g., Table 1 and FIG. 6).

As to the adjustment block 750 of the method 700 of FIG. 7, an adjustment may be made to input of one or more mercury porosimetry capillary pressure curves. As an example, pressure-volume adjustments computed in accordance with the computation block 740 may be applied to input mercury porosimetry capillary pressure curve(s) using arithmetic operations (e.g., add, multiply), as well via one or more mathematical transformation (e.g., depending on a method of adjustment determination, etc.).

As an example, an analysis framework may implement one or more techniques that can adjust information within a transition zone associated with a porosimeter (see, e.g., the GUI 410 of FIG. 4). For example, adjustments may be made depending on mercury porosimeter specifications and shape of input mercury porosimetry capillary pressure curve. As an example, one or more types of adjustments may be made, families of adjustments may be made, etc.

As to the output block 760, the method 700 of FIG. 7 may output a pressure-volume relationship that is adjusted based at least in part on one or more adjustments of the computation block 750. For example, the output block 760 may output a curve that spans a transition zone. Such a curve may be used, for example, to model one or more physical phenomena associated with one or more samples (e.g., core samples, etc.). As an example, the output block 760 may output information to memory, to a network interface, to a display, a printer, etc.

As an example, a method may be implemented that includes reshaping a curve, for example, where artifact points correspond to a jumping pressure on the plateau and/or where artifact points are visibly discernable because they correspond to a breaking slope. In such an example, the method can include receiving as input one or more mercury porosimetry capillary pressure curves and technical specifications (e.g., accuracy, transition capillary pressure, etc.) of a mercury porosimeter used to measure the one or more curves. The method may optionally perform artifact point detection automatically or, for example, with manual input (e.g., semi-automatically or manually). As an example, where results are not satisfactory, a user may manually specify a pressure range (e.g., along an X-axis) to focus a detection process within a certain zone.

Figure 13:
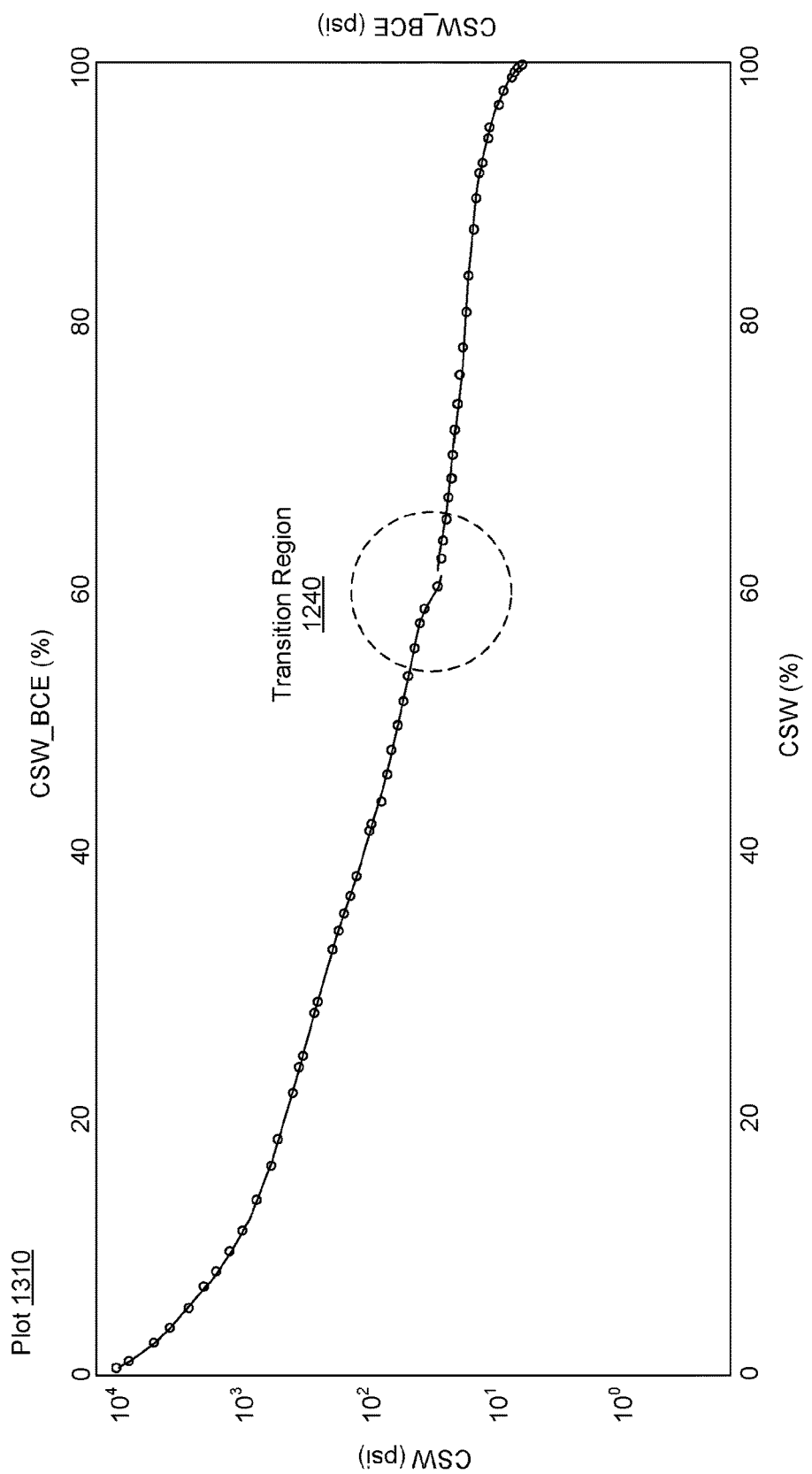
FIG. 13 illustrates an example of a plot.
Figure 14:
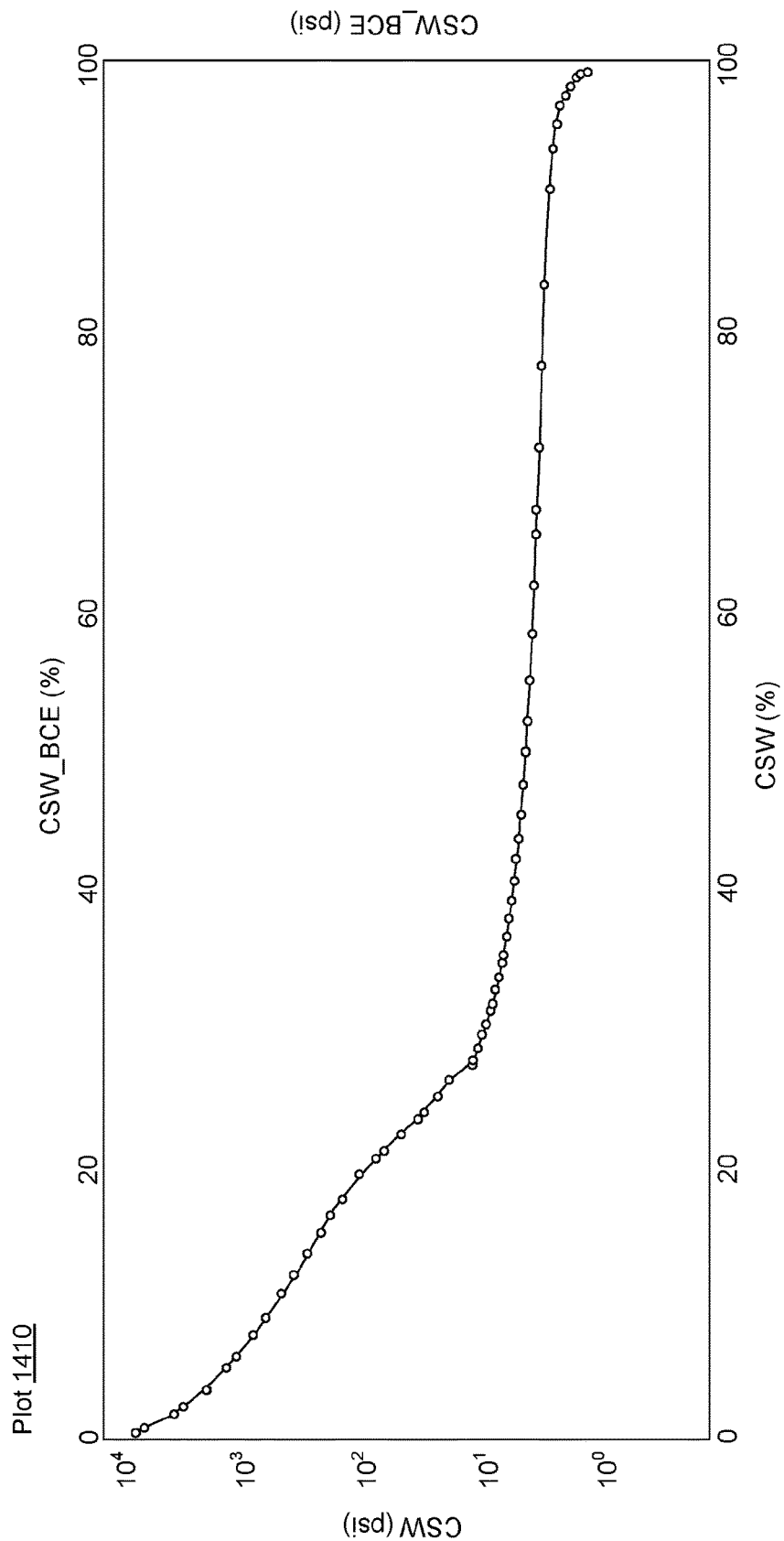
FIG. 14 illustrates an example of a plot.
Figure 15:
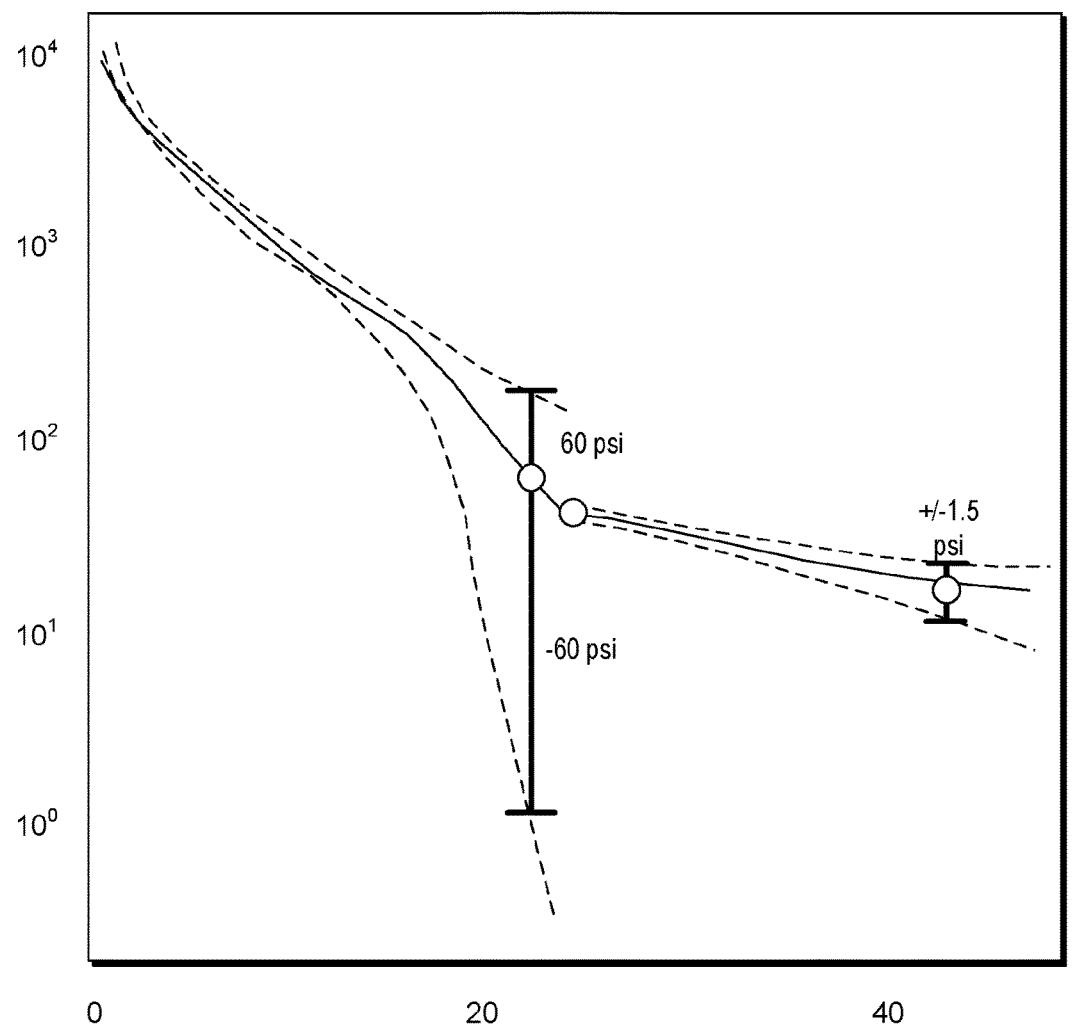
FIG. 15 illustrates an example of a plot.

FIGS. 13, 14 and 15 shows example plots 1310, 1410 and 1510. As an example, with reference to the plot 1310, a method can include receiving input for a range such as CSW=[50, 60]% as artifact points appear to correspond to a jumping pressure on the plateau; whereas, with reference to the plot 1410, a method can include receiving input for a range such as CSW=[23, 27]% as artifact points appear to correspond to a breaking slope. As to the plot 1410, as other artifacts are presented near to the effective artifact, a method may optionally include receiving input, for example, via a user to help make adjustments as to artifacts. As to the plot 1510, accuracy information is illustrated noting that the Y-axis is presented as a log axis, which causes the 60 psi accuracy value of the higher pressure zone above the data point to appear as a smaller distance than the 60 psi accuracy value of the high-pressure zone below the data point. Further, as indicated, for the lower pressure zone (e.g., low-pressure zone), the accuracy value is given as 1.5 psi above and below the data point. As an example, such accuracy information may be provided by a user, for example, into a data entry field of a GUI. As an example, a framework may include information for one or more porosimeters. As an example, a GUI may allow for selecting one of the porosimeters for which information exists, for entering information and associating it with a porosimeter, etc. As an example, data may include information (e.g., a header, etc.) that identifies a porosimeter and/or that specifies accuracy with respect to one or more pressure zones.

In the plot 1510, as shown, accuracy parameters are specified for each chamber. In such an example, a program may automatically calculate accuracy curves that can serve as limiting boundaries of one or more adjustments at least in part within a transition zone.

As an example, where an adjustment computation is made within the accuracy boundaries, if an adjusted curve does not respect the boundaries, the adjustment may be rejected (see, e.g., the plot 1110 of FIG. 11); whereas, if an adjusted curve is created within the accuracy boundaries, it may be validated (see, e.g., the plot 1210 of FIG. 12). As shown in the example plot 1210 of FIG. 12, an adjusted curve is the calculated adjusted curve falling inside the accuracy boundaries (see, e.g., envelop defined by dashed), which may thereby call for the adjustment to be accepted. As illustrated in FIG. 12, a method may fit input mercury porosimetry capillary pressure curve as best as possible to generate an adjusted curve that more closely adheres to physical reality.

As an example, a framework may present one or more adjusted curves to a display where, for example, they may be reviewed. As an example, an adjusted curve may be selected to be applied to one or more input mercury porosimetry capillary pressure curves.

As an example, an adjustment may be applied automatically, semi-automatically or manually. As an example, an adjusted curve may be rendered to a display with an original mercury porosimetry capillary pressure curve.

As an example, a method can include generating a verisimilar curve in terms of its shape and also in terms of accuracy and verisimilitude with reality, for example, because measurement accuracy of Hg pressure and Hg volume have been taken into account. An adjusted curve may be used in one or more target domains, such as hydrocarbon reservoir characterization workflows, including capillary pressure modeling, evaluating pore size and volume distributions, etc.

As an example, one or more adjusted curves, data resulting from an adjusted curve or curve, a model based at least in part on an adjusted curve may be used in a workflow. Such a workflow may include implementation of one or more features of a commercially available framework such as the PETREL® seismic to simulation software framework (Schlumberger Limited, Houston, Tex.). The PETREL® framework provides components that allow for optimization of exploration and development operations. The PETREL® framework includes seismic to simulation software components that can output information for use in increasing reservoir performance, for example, by improving asset team productivity. Through use of such a framework, various professionals (e.g., geophysicists, geologists, and reservoir engineers) can develop collaborative workflows and integrate operations to streamline processes. Such a framework may be considered an application and may be considered a data-driven application (e.g., where data is input for purposes of simulating a geologic environment).

In an example embodiment, one or more modules may be implemented as add-ons or plug-ins that operate according to specifications of a framework environment. For example, a commercially available framework environment marketed as the OCEAN® framework environment (Schlumberger Limited, Houston, Tex.) allows for seamless integration of add-ons (or plug-ins) into a PETREL® framework workflow. The OCEAN® framework environment leverages .NET® tools (Microsoft Corporation, Redmond, Wash.) and offers stable, user-friendly interfaces for efficient development. In an example embodiment, various components may be implemented as add-ons (or plug-ins) that conform to and operate according to specifications of a framework environment (e.g., according to application programming interface (API) specifications, etc.).

As an example, a module may be a module of an analysis framework such as, for example, the TECHLOG® analysis framework. As an example, an OCEAN® framework plug-in may be provided that allows interaction between the PETREL® framework and the TECHLOG® analysis framework. In such an example, the module may provide analysis results that can be communicated to the PETREL® framework. As an example, such results may include pore information, etc. As an example, the PETREL® framework may refine a model of a geologic environment based at least in part on pore information, for example, for purposes of simulation, etc.

As an example, a method can include receiving porosimetry data for a range of pressures that spans a transition zone defined at least in part by a high-pressure end of a first pressure zone and a low-pressure end of a second pressure zone; detecting at least one artifact in the transition zone; computing accuracy information for the high-pressure end of a first pressure zone and the low-pressure end of a second pressure zone; computing a pressure-volume adjustment based at least in part on the accuracy information; and outputting a pressure-volume relationship in the transition zone based at least in part on the pressure-volume adjustment. In such an example, the first pressure zone may be a low-pressure zone of a mercury porosimetry system and the second pressure zone may be a high-pressure zone of the mercury porosimetry system.

As an example, a method can include receiving porosimetry data that includes at least one pressure-volume curve. As an example, a method can include receiving pressure gauge information for at least one pressure gauge of a porosimeter. As an example, a method can include computing accuracy information in a manner that computes at least a portion of the accuracy information based at least in part on the received pressure gauge information.

As an example, porosimetry data can correspond to a sample. For example, a method may include receiving porosimetry data for a rock sample. Such a rock sample may be, for example, a reservoir rock sample. As an example, a sample may be a portion of a rock core.

As an example, a system can include a processor; memory accessible by the processor; modules stored in the memory that include processor-executable instructions that instruct the system to receive porosimetry data for a range of pressures that spans a transition zone defined at least in part by a high-pressure end of a first pressure zone and a low-pressure end of a second pressure zone; detect at least one artifact in the transition zone; compute accuracy information for the high-pressure end of a first pressure zone and the low-pressure end of a second pressure zone; compute a pressure-volume adjustment based at least in part on the accuracy information; and output a pressure-volume relationship in the transition zone based at least in part on the pressure-volume adjustment. In such an example, the system may include at least one module that includes processor-executable instructions to instruct the system to render a graphical user interface to a display. As an example, such a graphical user interface can include a graphical control to commence a capillary pressure data analysis that may, for example, reduce the effect of an artifact in the transition zone.

As an example, a system may include at least one module that includes processor-executable instructions to instruct the system to model pore structure of a sample based at least in part on the pressure-volume relationship.

As an example, in a system, a first pressure zone may be a low-pressure zone of a mercury porosimetry system and a second pressure zone may be a high-pressure zone of the mercury porosimetry system. As an example, porosimetry data can include at least one pressure-volume curve. For example, consider one or more curves that span multiple pressure zones.

As an example, a system can include at least one module that includes processor-executable instructions to instruct the system to receive pressure gauge information for at least one pressure gauge of a porosimeter. In such an example, the system can include instructions to compute accuracy information based at least in part on the received pressure gauge information.

As an example, one or more computer-readable storage media can include computer-executable instructions that include computer-executable instructions to instruct a computing system to: receive porosimetry data for a range of pressures that spans a transition zone defined at least in part by a high-pressure end of a first pressure zone and a low-pressure end of a second pressure zone; detect at least one artifact in the transition zone; compute accuracy information for the high-pressure end of a first pressure zone and the low-pressure end of a second pressure zone; compute a pressure-volume adjustment based at least in part on the accuracy information; and output a pressure-volume relationship in the transition zone based at least in part on the pressure-volume adjustment. In such an example, the first pressure zone can include a low-pressure zone of a mercury porosimetry system and the second pressure zone can include a high-pressure zone of the mercury porosimetry system.

As an example, one or more computer-readable media can include processor-executable instructions to instruct the system to receive pressure gauge information for at least one pressure gauge of a porosimeter and, for example, instructions to compute accuracy information based at least in part on the received pressure gauge information.

The term "circuit" or "circuitry" can include all levels of available integration, e.g., from discrete logic circuits to the highest level of circuit integration such as VLSI, and includes programmable logic components programmed to perform the functions of an embodiment as well as general-purpose or special-purpose processors programmed with instructions to perform those functions. Circuitry can include one or more computer-readable media that include computer-executable instructions to instruct a computer to perform one or more actions. The term "computer-executable instructions" includes processor-executable instructions, whether a processor is a central processor, a graphics processor or other type of processor. Instructions stored on a computer-readable medium may be software (e.g., instructions for telling a computer, computing device, etc., what to do and how to do it). A computer-readable medium may be a storage device such as memory, an optical storage device, etc. Such a storage device may store instructions and optionally other information (e.g., data, etc.) in a non-transitory manner.

FIG. 16 shows components of an example of a computing system 1600 and an example of a networked system 1610. The system 1600 includes one or more processors 1602, memory and/or storage components 1604, one or more input and/or output devices 1606 and a bus 1608. In an example embodiment, instructions may be stored in one or more computer-readable media (e.g., memory/storage components 1604). Such instructions may be read by one or more processors (e.g., the processor(s) 1602) via a communication bus (e.g., the bus 1608), which may be wired or wireless. The one or more processors may execute such instructions to implement (wholly or in part) one or more attributes (e.g., as part of a method). A user may view output from and interact with a process via an I/O device (e.g., the device 1606). In an example embodiment, a computer-readable medium may be a storage component such as a physical memory storage device, for example, a chip, a chip on a package, a memory card, etc. (e.g., a computer-readable storage medium).

In an example embodiment, components may be distributed, such as in the network system 1610. The network system 1610 includes components 1622-1, 1622-2, 1622-3, . . . , 1622-N. For example, the components 1622-1 may include the processor(s) 1602 while the component(s) 1622-3 may include memory accessible by the processor(s) 1602. Further, the component(s) 1602-2 may include an I/O device for display and optionally interaction with a method. The network may be or include the Internet, an intranet, a cellular network, a satellite network, etc.

As an example, a device may be a mobile device that includes one or more network interfaces for communication of information. For example, a mobile device may include a wireless network interface (e.g., operable via IEEE 802.11, ETSI GSM, BLUETOOTH®, satellite, etc.). As an example, a mobile device may include components such as a main processor, memory, a display, display graphics circuitry (e.g., optionally including touch and gesture circuitry), a SIM slot, audio/video circuitry, motion processing circuitry (e.g., accelerometer, gyroscope), wireless LAN circuitry, smart card circuitry, transmitter circuitry, GPS circuitry, and a battery. As an example, a mobile device may be configured as a cell phone, a tablet, etc. As an example, a method may be implemented (e.g., wholly or in part) using a mobile device. As an example, a system may include one or more mobile devices.

As an example, a system may be a distributed environment, for example, a so-called "cloud" environment where various devices, components, etc. interact for purposes of data storage, communications, computing, etc. As an example, a device or a system may include one or more components for communication of information via one or more of the Internet (e.g., where communication occurs via one or more Internet protocols), a cellular network, a satellite network, etc. As an example, a method may be implemented in a distributed environment (e.g., wholly or in part as a cloud-based service).

As an example, information may be input from a display (e.g., consider a touchscreen), output to a display or both. As an example, information may be output to a projector, a laser device, a printer, etc. such that the information may be viewed. As an example, information may be output stereographically or holographically. As to a printer, consider a 2D or a 3D printer. As an example, a 3D printer may include one or more substances that can be output to construct a 3D object. For example, data may be provided to a 3D printer to construct a 3D representation of a subterranean formation. As an example, layers may be constructed in 3D (e.g., horizons, etc.), geobodies constructed in 3D, etc. As an example, holes, fractures, etc., may be constructed in 3D (e.g., as positive structures, as negative structures, etc.).

Although only a few example embodiments have been described in detail above, those skilled in the art will readily appreciate that many modifications are possible in the example embodiments. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words "means for" together with an associated function.

What is claimed is:

1. A method comprising:
receiving porosimetry data for a range of pressures that spans a transition zone defined at least in part by a high-pressure end of a first pressure zone and a low-pressure end of a second pressure zone;
detecting at least one artifact in the transition zone;
computing accuracy information for the high-pressure end of the first pressure zone and the low-pressure end of the second pressure zone;
computing a pressure-volume adjustment based at least in part on the accuracy information; and
outputting a pressure-volume relationship in the transition zone based at least in part on the pressure-volume adjustment.

2. The method of claim 1 wherein the first pressure zone comprises a low-pressure zone of a mercury porosimetry system and wherein the second pressure zone comprises a high-pressure zone of the mercury porosimetry system.

3. The method of claim 1 wherein the porosimetry data comprise at least one pressure-volume curve.

4. The method of claim 1 further comprising receiving pressure gauge information for at least one pressure gauge of a porosimeter.

5. The method of claim 4 wherein the computing accuracy information computes at least a portion of the accuracy information based at least in part on the received pressure gauge information.

6. The method of claim 1 wherein the porosimetry data corresponds to a sample.

7. The method of claim 6 wherein the sample comprises a rock sample.

8. The method of claim 7 wherein the rock sample comprises a reservoir rock sample.

9. The method of claim 6 wherein the sample comprises a portion of a rock core.

10. A system comprising:
a processor;
memory accessible by the processor;
modules stored in the memory that comprise processor-executable instructions that instruct the system to
receive porosimetry data for a range of pressures that spans a transition zone defined at least in part by a high-pressure end of a first pressure zone and a low-pressure end of a second pressure zone;
detect at least one artifact in the transition zone;
compute accuracy information for the high-pressure end of the first pressure zone and the low-pressure end of the second pressure zone;
compute a pressure-volume adjustment based at least in part on the accuracy information; and output a pressure-volume relationship in the transition zone based at least in part on the pressure-volume adjustment.

11. The system of claim 10 comprising at least one module that comprises processor-executable instructions to instruct the system to render a graphical user interface to a display.

12. The system of claim 11 wherein the graphical user interface comprises a graphical control to commence a capillary pressure data analysis.

13. The system of claim 11 wherein the graphical user interface comprises a graphical control to commence a capillary pressure data analysis that reduces the effect of an artifact in the transition zone.

14. The system of claim 10 comprising at least one module that comprises processor-executable instructions to instruct the system to model pore structure of a sample based at least in part on the pressure-volume relationship.

15. The system of claim 10 wherein the first pressure zone comprises a low-pressure zone of a mercury porosimetry system and wherein the second pressure zone comprises a high-pressure zone of the mercury porosimetry system.

16. The system of claim 10 wherein the porosimetry data comprise at least one pressure-volume curve.

17. The system of claim 10 further comprising at least one module that comprises processor-executable instructions to instruct the system to receive pressure gauge information for at least one pressure gauge of a porosimeter and wherein the instructions to compute accuracy information compute at least a portion of the accuracy information based at least in part on the received pressure gauge information.

18. One or more computer-readable storage media comprising computer-executable instructions that comprise computer-executable instructions to instruct a computing system to:
receive porosimetry data for a range of pressures that spans a transition zone defined at least in part by a high-pressure end of a first pressure zone and a low-pressure end of a second pressure zone;
detect at least one artifact in the transition zone;
compute accuracy information for the high-pressure end of the first pressure zone and the low-pressure end of the second pressure zone;
compute a pressure-volume adjustment based at least in part on the accuracy information; and
output a pressure-volume relationship in the transition zone based at least in part on the pressure-volume adjustment.

19. The one or more computer-readable media of claim 18 wherein the first pressure zone comprises a low-pressure zone of a mercury porosimetry system and wherein the second pressure zone comprises a high-pressure zone of the mercury porosimetry system.

20. The one or more computer-readable media of claim 18 further comprising processor-executable instructions to instruct the system to receive pressure gauge information for at least one pressure gauge of a porosimeter and wherein the instructions to compute accuracy information compute at least a portion of the accuracy information based at least in part on the received pressure gauge information.

* * * * *